US011883245B2

(12) United States Patent
Fathollahi Ghezelghieh et al.

(10) Patent No.: US 11,883,245 B2
(45) Date of Patent: Jan. 30, 2024

(54) DEEP-LEARNING-BASED REAL-TIME REMAINING SURGERY DURATION (RSD) ESTIMATION

(71) Applicant: Verb Surgical Inc., Santa Clara, CA (US)

(72) Inventors: Mona Fathollahi Ghezelghieh, Sunnyvale, CA (US); Jocelyn Elaine Barker, San Jose, CA (US); Pablo Eduardo Garcia Kilroy, Menlo Park, CA (US)

(73) Assignee: VERB SURGICAL INC., Santa Clara, CA (US)

( * ) Notice: Subject to any disclaimer, the term of this patent is extended or adjusted under 35 U.S.C. 154(b) by 485 days.

(21) Appl. No.: 17/208,715

(22) Filed: Mar. 22, 2021

(65) Prior Publication Data
US 2022/0296334 A1 Sep. 22, 2022

(51) Int. Cl.
*A61B 90/00* (2016.01)
*G06N 3/08* (2023.01)
(Continued)

(52) U.S. Cl.
CPC ............. *A61B 90/37* (2016.02); *G06N 3/047* (2023.01); *G06N 3/08* (2013.01); *G16H 10/00* (2018.01)

(58) Field of Classification Search
CPC . A61B 90/37; A61B 2090/371; A61B 90/361; A61B 34/30; G06N 3/047;
(Continued)

(56) References Cited

U.S. PATENT DOCUMENTS

| 8,846,034 B2 * | 9/2014 | Jiang | A61K 47/10 424/94.62 |
| 2006/0079752 A1 * | 4/2006 | Anderl | A61B 90/36 600/407 |

(Continued)

FOREIGN PATENT DOCUMENTS

KR 10-2013828 8/2019

OTHER PUBLICATIONS

International Search Report and Written Opinion for International Application No. PCT/IB2022/050386 dated Apr. 15, 2022, 8 pages.
(Continued)

*Primary Examiner* — Ali Bayat
(74) *Attorney, Agent, or Firm* — Aikin & Gallant, LLP

(57) ABSTRACT

Embodiments described herein provide a surgical duration estimation system for continuously predicting real-time remaining surgical duration (RSD) of a live surgical session of a given surgical procedure based on a real-time endoscope video of the live surgical session. In one aspect, the process receives a current frame of the endoscope video at a current time of the live surgical session, wherein the current time is among a sequence of prediction time points for making continuous RSD predictions during the live surgical session. The process next randomly samples N−1 additional frames of the endoscope video corresponding to the elapsed portion of the live surgical session between the beginning of the endoscope video corresponding to the beginning of the live surgical session and the current frame corresponding to the current time. The process then combines the N−1 randomly sampled frames and the current frame in the temporal order to obtain a set of N frames. Next, the process feeds the set of N frames into a trained model for the given surgical procedure. The process subsequently outputs a current RSD prediction based on the set of N frames.

20 Claims, 7 Drawing Sheets

(51) Int. Cl.
*G06N 3/047* (2023.01)
*G16H 10/00* (2018.01)

(58) Field of Classification Search
CPC ...... G06N 3/08; G06N 3/0442; G06N 3/0464; G06N 3/09; G06N 3/0895; G16H 10/00
USPC ........................................................ 382/159
See application file for complete search history.

(56) References Cited

U.S. PATENT DOCUMENTS

| | | | | |
|---|---|---|---|---|
| 2008/0059070 | A1* | 3/2008 | Boyden | A61B 18/20 250/492.1 |
| 2012/0308484 | A1* | 12/2012 | Szalay | A61P 43/00 424/9.4 |
| 2019/0223961 | A1 | 7/2019 | Barral et al. | |
| 2020/0194111 | A1 | 6/2020 | Venkataraman et al. | |
| 2021/0059503 | A1* | 3/2021 | Tanaka | A61B 1/00045 |
| 2022/0104887 | A1* | 4/2022 | Hufford | A61B 90/37 |
| 2022/0202508 | A1* | 6/2022 | Hiranandani | G06N 20/00 |

OTHER PUBLICATIONS

Twinanda, A.P., et al., "RSDNet: Learning to Predict Remaining Surgery Duration from Laparoscopic Videos Without Manual Annotations," IEEE Transactions on Medical Imaging, Apr. 2019, vol. 38, No. 4, pp. 1069-1078.

Aksamentov, I., et al., "Deep Neural Networks Predict Remaining Surgery Duration from Cholecystectomy Videos," International Conference on Medical Image Computing and Computer Assisted Intervention, Conference paper, Sep. 4, 2017, MICCAI 2017, Part II, LNCS 10434, pp. 586-593.

Guedon, A.C. P., et al., "Deep learning for surgical phase recognition using endoscopic videos," Surgical Endoscopy, 2021, Published online Nov. 25, 2020, vol. 35, pp. 6150-6157.

* cited by examiner

DEEP-LEARNING-BASED REAL-TIME REMAINING SURGERY DURATION (RSD) ESTIMATION

TECHNICAL FIELD

The present disclosure generally relates to building machine-learning-based surgical procedure analysis tools and, more specifically, to systems, devices and techniques for performing deep-learning-based real-time remaining surgery duration (RSD) estimations during a live surgical session of a surgical procedure based on endoscopy video feed.

BACKGROUND

Operating room (OR) costs are among one of the highest medical and healthcare-related costs. With skyrocketing healthcare expenditures, OR-costs management aimed at reducing OR costs and increasing OR efficiency has become an increasingly important research subject. OR costs are often measured based on a per-minute cost structure. For example, one 2005 study shows that the OR costs range from $22 to $133 per minute with an average cost of $62 per minute. In this per-minute cost structure, the OR costs of a given surgical procedure are directly proportional to the duration/length of the surgical procedure. Hence, accurate surgery duration estimation plays an important role in building an efficient OR management system. Note that if the OR team overestimate the surgery duration, it would lead to underutilization of expensive OR resources. On the other hand, if the surgery duration is underestimated, it would cause high waiting times for other OR teams and patients. However, it is very challenging to accurately predict surgery duration due to the diversity of patients, surgeon's skills and other unpredictable factors.

One solution to above problem is to use machine learning to automatically estimate remaining surgery duration (RSD) from laparoscopic video feed. For example, an existing RSD estimation technique manually labels each frame of a training dataset with pre-defined surgical phases. A supervised machine learning model is then trained based on the training dataset to estimate a surgical phase at each timestamp in the training dataset. Next, by utilising the statistics of each surgical phase across the training dataset, the time left to finish the current surgical phase can be estimated. This estimation combined with estimating what phases have been completed at the current timestamp is used to estimate RSD. Unfortunately, this technique requires manually labeling each of the frames in the training set, which is both labor-intensive and expensive.

Another existing RSD estimation technique is not dependent on surgical phase annotation. In this approach, the input to the machine learning model is a single frame. However, it is extremely difficult for the machine learning model to predict what has happened prior to the single frame just from the single frame itself. To fix this problem, different variations of recurrent neural network are utilized in an unsupervised approach to implicitly encapsulate the previous frames into a hidden state. Unfortunately, the RSD prediction accuracy of this approach is still poor because surgical videos are usually quite long and it is not trivial to teach a machine learning model to represent thousands of frames as multiple hidden states.

SUMMARY

Some embodiments described herein provide various examples of a surgical duration estimation system for continuously predicting in real-time a remaining surgical duration (RSD) of a live surgical session of a given surgical procedure based on a real-time endoscope video of the live surgical session. In a particular embodiment, a disclosed RSD-prediction system receives a current frame of the endoscope video at a current time of the live surgical session, wherein the current time is among a sequence of prediction time points for making continuous RSD predictions during the live surgical session. The RSD-prediction system next randomly samples N−1 additional frames of the endoscope video corresponding to the elapsed portion of the live surgical session between the beginning of the endoscope video corresponding to the beginning of the live surgical session and the current frame corresponding to the current time. The RSD-prediction system then combines the N−1 randomly sampled frames and the current frame in the temporal order to obtain a set of N frames. Next, the system feeds the set of N frames into a trained machine learning model for the given surgical procedure. The RSD-prediction system subsequently outputs a current RSD prediction based on the set of N frames.

In some embodiments, N is chosen to be sufficiently large so that the N−1 randomly-sampled frames provide a sufficiently accurate snapshot of various events that have occurred during the elapsed portion of the live surgical session.

In some embodiments, randomly sampling the elapsed portion of the live surgical session allows for sampling a given frame in the endoscope video more than once at different prediction time points while making continuous RSD predictions.

In some embodiments, the RSD-prediction system also generates a prediction of a percentage of completion of the live surgical session using the trained RSD ML model based on the set of N frames.

In some embodiments, the RSD-prediction system improves the current RSD prediction at the current time by repeating the following steps multiple times to generate a set of current RSD predictions: (1) randomly sampling N−1 additional frames of the endoscope video corresponding to the elapsed portion of the live surgical session between the beginning of the endoscope video corresponding to the beginning of the live surgical session and the current frame corresponding to the current time; combining the N−1 randomly sampled frames and the current frame in the temporal order to obtain a set of N frames; feeding the set of N frames into a trained RSD ML model; and generating a current RSD prediction from the trained RSD ML model based on the set of N frames. Next, the RSD-prediction system computes an average value and a variance value of the set of current RSD predictions. Subsequently, the RSD-prediction system improves the current RSD prediction by using the computed average and variance values as the current RSD prediction.

In some embodiments, the RSD-prediction system further improves the RSD predictions by: generating a continuous sequence of real-time RSD predictions corresponding to the sequence of prediction time points in the endoscope video; and applying a low-pass filter to the sequence of real-time RSD predictions to smooth out the RSD predictions by removing high frequency jitters in the sequence of real-time RSD predictions.

In some embodiments, the RSD-prediction system generates a training dataset by first receiving a set of training videos of the surgical procedure, wherein each video in the set of training videos corresponds to an execution of the surgical procedure performed by a surgeon skilled in the surgical procedure. Next, for each training video in the set of training videos, the RSD-prediction system constructs a set of labeled training data by performing a sequence of training data generation steps at a sequence of equally-spaced time points throughout the training video according to a predetermined time-interval. More specifically, each training data generation step in the sequence of training data generation steps at a corresponding time point in the sequence of time points includes: (1) receiving a current frame of the training video at the corresponding time point; (2) randomly sampling N−1 additional frames of the training video corresponding to the elapsed portion of the surgical session between the beginning of the training video and the current frame; (3) combining the N−1 randomly sampled frames and the current frame in the temporal order to obtain a set of N frames; an (4) labeling the set of N frames with a label associated with the current frame. Finally, the RSD-prediction system outputs multiple sets of labeled training data associated with the set of training videos.

In some embodiments, the RSD-prediction system establishes the trained RSD ML model by: (1) receiving a convolutional neural network (CNN) model; (2) training the CNN model with the training dataset comprising the multiple sets of labeled training data; and (3) obtaining the trained RSD ML model based on the trained CNN model.

In some embodiments, prior to generating the training dataset, the RSD-prediction system is further configured to label each training video in the set of training videos by: for each video frame in the training video, automatically determining a remaining surgical duration from the video frame to the end of the training video; and automatically annotating the video frame with the determined remaining surgical duration as the label of the video frame.

In some embodiments, the label associated with the current frame includes an associated remaining surgical duration in minutes.

In some embodiments, the CNN model includes an action recognition network architecture (I3d) configured to receive a sequence of video frames as a single input.

In some embodiments, training the CNN model with the training dataset includes evaluating the CNN model on a validation dataset.

Some embodiments described herein also provide various examples of a RSD-prediction model training system for constructing a trained RSD-prediction model for making real-time RSD predictions. In a particular embodiment, a disclosed RSD-prediction model training system receives a set of training videos of a target surgical procedure performed by a number of surgeons who can perform the target surgical procedure in a similar manner. Next, the disclosed model training system randomly selects a subset of training videos from the set of received training videos based on the computational resource restrictions. The disclosed model training system subsequently begins an iterative model tuning procedure based on the subset of training videos. Specifically, in each given iteration, the disclosed model training system selects, from each of the subset of training videos, a timestamp between the beginning and the end of the given training video. Subsequently, the disclosed model training system extracts a video frame in each of the subset of training videos based on the set of randomly-selected timestamps.

Next, for each randomly-selected video frame in each of the subset of training videos, the disclosed model training system constructs a set of N-frames for the given video frame in the corresponding training video by: randomly sampling N−1 additional frames of the training video between the beginning of the training video and the randomly-selected video frame; and combining the N−1 randomly-sampled frames and the randomly-selected video frame in the temporal order. In this manner, the disclosed model training system generates a batch of training data comprising sets of N-frames extracted from the subset of training videos. Subsequently, the disclosed model training system uses the batch of training data to update the model parameters of the RSD-prediction model. Next, the disclosed model training system evaluates the updated RSD-prediction model on a validation dataset to determine whether another iteration of the model training process is needed. We now describe different embodiments of the real-time RSD-prediction system and the RSD-prediction model training system in more detail below.

In some embodiments, the RSD-prediction model training system is configured to train the RSD-prediction model using multiple sets of labeled training data corresponding to the set of training videos. More specifically, the RSD-prediction model is configured to train the RSD-prediction model by: randomly selecting one labeled training data from each set of labeled training data in the multiple sets of labeled training data; combining the set of randomly-selected labeled training data to form a batch of training data; and training the RSD-prediction model with the batch of training data to update the RSD-prediction model.

BRIEF DESCRIPTION OF THE DRAWINGS

The structure and operation of the present disclosure will be understood from a review of the following detailed description and the accompanying drawings in which like reference numerals refer to like parts and in which.

DETAILED DESCRIPTION

Figure 1:
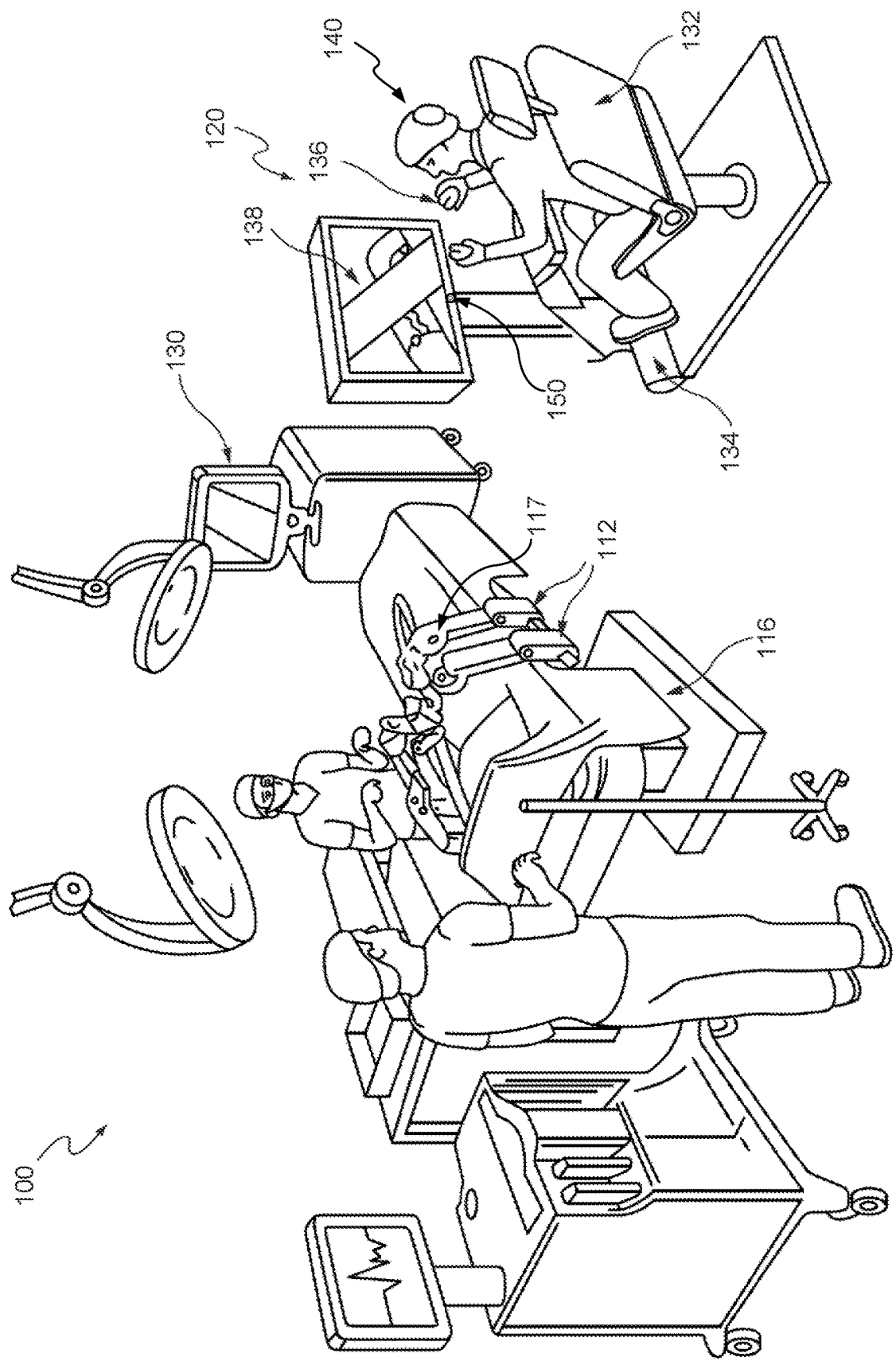
FIG. 1 shows a diagram illustrating an exemplary operating room (OR) environment with a robotic surgical system in accordance with some embodiments described herein.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, the subject technology is not limited to the specific details set forth herein and may be practiced without these specific details. In some instances, structures and components are shown in block diagram form in order to avoid obscuring the concepts of the subject technology.

Some embodiments described herein provide various examples of a surgical duration estimation system for continuously predicting in real-time a remaining surgical duration (RSD) of a live surgical session of a given surgical procedure based on a real-time endoscope video of the live surgical session. In a particular embodiment, a disclosed RSD-prediction system receives a current frame of the endoscope video at a current time of the live surgical session, wherein the current time is among a sequence of prediction time points for making continuous RSD predictions during the live surgical session. The RSD-prediction system next randomly samples N−1 additional frames of the endoscope video corresponding to the elapsed portion of the live surgical session between the beginning of the endoscope video corresponding to the beginning of the live surgical session and the current frame corresponding to the current time. The RSD-prediction system then combines the N−1 randomly sampled frames and the current frame in the temporal order to obtain a set of N frames. Next, the system feeds the set of N frames into a trained machine learning model for the given surgical procedure. The RSD-prediction system subsequently outputs a current RSD prediction based on the set of N frames.

Some embodiments described herein also provide various examples of a RSD-prediction model training system for constructing a trained RSD-prediction model for making real-time RSD predictions. In a particular embodiment, a disclosed RSD-prediction model training system receives a set of training videos of a target surgical procedure performed by a number of surgeons who can perform the target surgical procedure in a similar manner. Next, the disclosed model training system randomly selects a subset of training videos from the set of received training videos based on the computational resource restrictions. The disclosed model training system subsequently begins an iterative model tuning procedure based on the subset of training videos. Specifically, in each given iteration, the disclosed model training system selects, from each of the subset of training videos, a timestamp between the beginning and the end of the given training video. Subsequently, the disclosed model training system extracts a video frame in each of the subset of training videos based on the set of randomly-selected timestamps.

Next, for each randomly-selected video frame in each of the subset of training videos, the disclosed model training system constructs a set of N-frames for the given video frame in the corresponding training video by: randomly sampling N−1 additional frames of the training video between the beginning of the training video and the randomly-selected video frame; and combining the N−1 randomly-sampled frames and the randomly-selected video frame in the temporal order. In this manner, the disclosed model training system generates a batch of training data comprising sets of N-frames extracted from the subset of training videos. Subsequently, the disclosed model training system uses the batch of training data to update the model parameters of the RSD-prediction model. Next, the disclosed model training system evaluates the updated RSD-prediction model on a validation dataset to determine whether another iteration of the model training process is needed. We now describe different embodiments of the real-time RSD-prediction system and the RSD-prediction model training system in more detail below.

FIG. 1 shows a diagram illustrating an exemplary operating room (OR) environment 110 with a robotic surgical system 100 in accordance with some embodiments described herein. As shown in FIG. 1, robotic surgical system 100 comprises a surgeon console 120, a control tower 130, and one or more surgical robotic arms 112 located at a robotic surgical platform 116 (e.g., a table or a bed, etc.), where surgical tools with end effectors are attached to the distal ends of the robotic arms 112 for executing a surgical procedure. The robotic arms 112 are shown as a table-mounted system, but in other configurations, the robotic arms may be mounted in a cart, ceiling or sidewall, or other suitable support surface. Robotic surgical system 100 can include any currently existing or future-developed robot-assisted surgical systems for performing robot-assisted surgeries.

Generally, a user/operator 140, such as a surgeon or other operator, may use the user console 120 to remotely manipulate the robotic arms 112 and/or surgical instruments (e.g., tele-operation). User console 120 may be located in the same operating room as robotic surgical system 100, as shown in FIG. 1. In other environments, user console 120 may be located in an adjacent or nearby room, or tele-operated from a remote location in a different building, city, or country. User console 120 may comprise a seat 132, foot-operated controls 134, one or more handheld user interface devices (UIDs) 136, and at least one user display 138 configured to display, for example, a view of the surgical site inside a patient. As shown in the exemplary user console 120, a surgeon located in the seat 132 and viewing the user display 138 may manipulate the foot-operated controls 134 and/or UIDs 136 to remotely control the robotic arms 112 and/or surgical instruments mounted to the distal ends of the arms.

In some variations, a user may also operate robotic surgical system 100 in an "over the bed" (OTB) mode, in which the user is at the patient's side and simultaneously manipulating a robotically driven tool/end effector attached thereto (e.g., with a handheld user interface device (UID) 136 held in one hand) and a manual laparoscopic tool. For example, the user's left hand may be manipulating a handheld UID 136 to control a robotic surgical component, while the user's right hand may be manipulating a manual laparoscopic tool. Thus, in these variations, the user may perform both robotic-assisted (minimally invasive surgery) MIS and manual laparoscopic surgery on a patient.

During an exemplary procedure or surgery, the patient is prepped and draped in a sterile fashion to receive anesthesia. Initial access to the surgical site may be performed manually with robotic surgical system 100 in a stowed or withdrawn configuration to facilitate access to the surgical site. Once the access is completed, initial positioning and/or preparation of the robotic system may be performed. During the procedure, a surgeon in the user console 120 may utilize the foot-operated controls 134 and/or UIDs 136 to manipulate various surgical tools/end effectors and/or imaging systems to perform the surgery. Manual assistance may also be provided at the procedure table by sterile-gowned personnel, who may perform tasks including but not limited to, retracting tissues or performing manual repositioning or tool exchange involving one or more robotic arms 112. Non-sterile personnel may also be present to assist the surgeon at the user console 120. When the procedure or surgery is completed, robotic surgical system 100 and/or user console 120 may be configured or set in a state to facilitate one or more post-operative procedures, including but not limited to, robotic surgical system 100 cleaning and/or sterilization, and/or healthcare record entry or printout, whether electronic or hard copy, such as via the user console 120.

In some aspects, the communication between robotic surgical platform 116 and user console 120 may be through control tower 130, which may translate user commands from the user console 120 to robotic control commands and transmit the robotic control commands to robotic surgical platform 116. Control tower 130 may also transmit status and feedback from robotic surgical platform 116 back to user console 120. The connections between robotic surgical platform 116, user console 120 and control tower 130 can be via wired and/or wireless connections, and can be proprietary and/or performed using any of a variety of data communication protocols. Any wired connections may be optionally built into the floor and/or walls or ceiling of the operating room. Robotic surgical system 100 can provide video output to one or more displays, including displays within the operating room as well as remote displays accessible via the Internet or other networks. The video output or feed may also be encrypted to ensure privacy and all or portions of the video output may be saved to a server or electronic healthcare record system.

Figure 2:
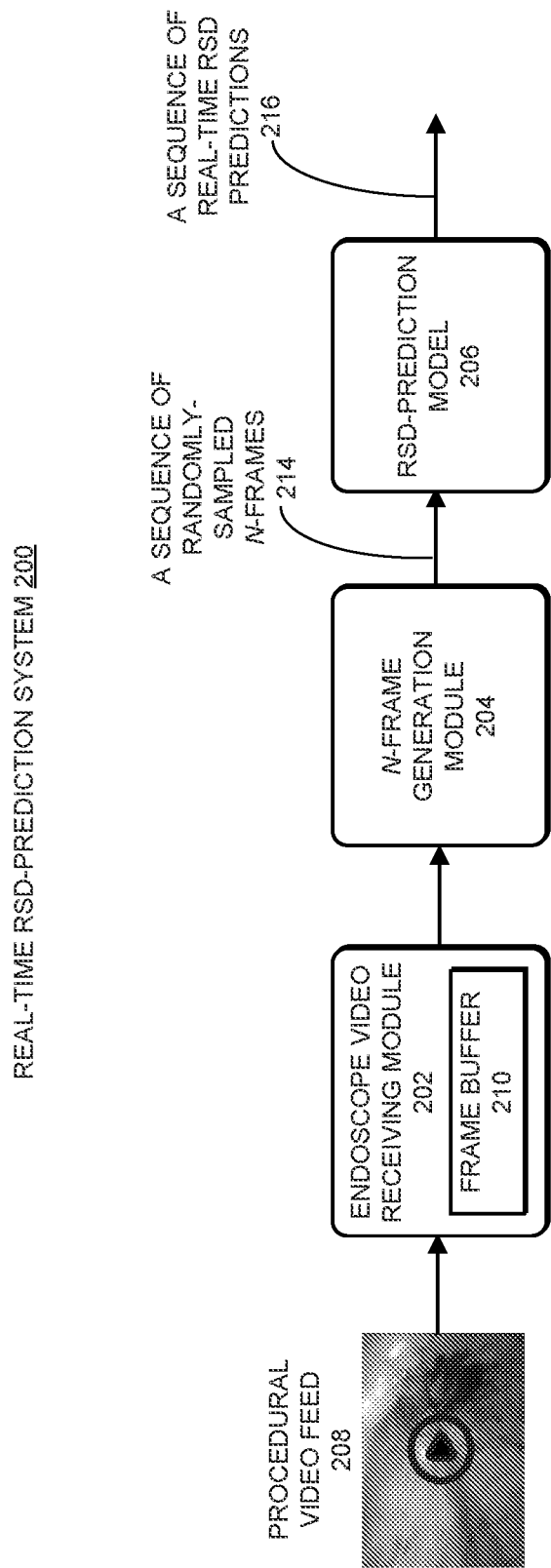
FIG. 2 illustrates a block diagram of a remaining surgical duration (RSD)-prediction system for performing real-time RSD predictions during a surgical procedure based on a procedural video feed in accordance with some embodiments described herein.

FIG. 2 illustrates a block diagram of a remaining surgical duration (RSD)-prediction system 200 for performing real-time RSD predictions during a surgical procedure based on a procedural video feed in accordance with some embodiments described herein. As shown in FIG. 2, RSD-prediction system 200 can include an endoscope video receiving module 202, an N-frame generation module 204, and a trained RSD-prediction machine-learning (ML) model 206, which are coupled in the manner shown. However, other embodiments of the disclosed RSD-prediction system may include additional processing modules between endoscope video receiving module 202 and trained RSD-prediction ML model 206 (or "RSD-prediction model 206" hereinafter) not shown in FIG. 2.

In some embodiments, RSD-prediction model 206 was specifically constructed and trained for a particular surgical procedure, e.g., a Roux-en-Y gastric bypass procedure or a sleeve gastrectomy procedure. Note that this particular surgical procedure typically includes a set of predetermined phases/steps (and each phases/step may additionally include subphases/substeps) which is characteristic of the particular surgical procedure. In some embodiments, endoscope video receiving module 202 in RSD-prediction system 200 receives a real-time/live endoscope video feed 208 of the surgical procedure, e.g., a gastric bypass procedure being performed by a surgeon. In some embodiments, in order to provide complete and continuous RSD predictions during the surgical procedure, endoscope video receiving module 202 can receive live endoscope video feed 208 (or "video feed 208" hereinafter) of the surgical procedure in its entirety, i.e., from the very beginning of the surgical procedure until the end of the surgical procedure. Note that video feed 208 is typically composed of unprocessed raw video images mostly captured from inside the patient's body.

A person skilled in the art would appreciate that multiple trained RSD-prediction models can be constructed/built prior to performing real-time RSD predictions, such that each RSD-prediction model in the multiple trained RSD-prediction models is constructed for a specific surgical procedure among multiple different surgical procedures. Hence, based on the specific surgical procedure captured by video feed 208, RSD-prediction system 200 can select a corresponding RSD-prediction model 206 from the multiple constructed RSD-prediction models to be used by RSD-prediction system 200.

In some embodiments, endoscope video receiving module 202 further includes a frame buffer 210 of a predetermined buffer size. Note that at the beginning of the surgical procedure when video feed 208 has just started being received, frame buffer 210 is essentially empty so that every frame or every other frame in the received video feed 208 can be buffered in frame buffer 210. However, the predetermined buffer size of frame buffer 210 is often smaller than the space required to store each and every frame or even every other frame of an entire recorded video feed. As such, in some embodiments, frame buffer 210 can be configured as a rolling buffer. In these embodiments, when frame buffer 210 becomes full at certain point during the live surgical procedure, endoscope video receiving module 202 may be configured to receive and store a new video frame from the endoscope feed 208 into frame buffer 210 and at the same time, remove an older video frame, e.g., the oldest frame from frame buffer 210. We will describe frame buffer 210 management in more detail below.

RSD-prediction system 200 further includes an N-frame generation module 204 which is coupled to endoscope video receiving module 202. In some embodiments, N-frame generation module 204 is configured to operate on every time point corresponding to each newly received video frame. This means that if video feed 208 is captured at 60 fps, N-frame generation module 204 is activated 60 times/sec by each and every received frame. However, this approach can be highly computationally intensive and impractical. In some other embodiments, N-frame generation module 204 may be synchronized to a timer so that N-frame generation module 204 is only triggered/activated at a series of predetermined time points according to a predetermined time interval, e.g., at every 1-second, 2-second, or 5-second, etc. This means that if video feed 208 is captured at 60 fps, N-frame generation module 204 is only activated once every 60 frames, 120 frames, or 300 frames, etc., instead at every single frame.

Because RSD-prediction system 200 is configured to generate continuous and real-time RSD predictions/updates during a live surgical procedure, we refer to the time corresponding to each RSD prediction point as the "current time," "current time T" or "current time point" of the live surgical procedure, regardless of whether the RSD predictions are made on the per frame basis or based on a predetermined time interval. However, if the RSD predictions are made based on the predetermined time interval, e.g., every 1-second or 2-second, the current time point for making a current RSD prediction is among a sequence of predetermined time points for making continuous RSD predictions/updates during the entire surgical procedure. Moreover, we refer to the video frame of the video feed 208 corresponding to the current time point as the "current frame" of the live surgical procedure, which is also the newest video frame in video feed 208.

In some embodiments, in preparation for generating a real-time RSD prediction, N-frame generation module 204 obtains the current frame of endoscope feed 208 at the current time of the surgical procedure. Note that N-frame generation module 204 can obtain the current frame from frame buffer 210 in endoscope video receiving module 202 or directly from video feed 208. Moreover, N-frame generation module 204 is configured to randomly sample N−1 additional frames from the previously received and stored video frames of video feed 208 corresponding to the elapsed portion of the surgical procedure, i.e., from the beginning of the endoscope video corresponding to the beginning of the surgical procedure until the current frame of video feed 208 corresponding to the current time point. Note that N herein is a predetermined integer number to be described below in more detail.

In some embodiments, integer number N is chosen as a trade-off between the computational constraints for RSD-prediction system 200 to process the set of N-frames (which dictates an upper limit of N) and a sufficiently large set of N−1 randomly-sampled frames from the elapsed portion of the surgical procedure to provide a representative or a sufficiently accurate snapshot of a set of events that have taken place during the elapsed portion of the surgical procedure (which dictates a lower limit of N). In this manner, the downstream RSD-prediction model 206 can predict at which time point and phase/step the current frame is located in the overall surgical procedure based on analyzing the set of images captured by N−1 randomly-sampled frames and the current frame (i.e., a total of N frames). On the other hand, the upper limit of number N dictates that the set of N-frames can be processed in real-time within the predetermined time interval to make a real-time RSD prediction by the downstream RSD-ML model 206.

Note that N-frame generation module 204 can randomly sample the N−1 frames from the buffered video frames in frame buffer 210. For example, if at the current time T, a total of K frames are buffered/stored in frame buffer 210 (including the current frame), then the N−1 frames can be randomly sampled among the K−1 frames (excluding the current frame). Note that for practical reasons, we want $(N-1)<=(K-1)$. In some embodiments, N is a number between [4, 20]. Hence, after the initial few seconds of receiving and buffering video frames from the endoscope feed 208, the relationship $(N-1)<<(K-1)$ can be easily satisfied and subsequently maintained throughout the entirely surgical procedure.

In some embodiments, each video frame in frame buffer 210 is associated with a corresponding sequence number s representing the order that the video frame is received by receiving module 202. For example, if at the current time, a total of K frames have been received, then each stored frame in frame buffer 210 will have a corresponding sequence number s from 1 to K (with K being the current frame). Hence, to randomly sample N−1 frames among the K−1 buffered frames, N-frame generation module 204 can generate a first random number $R_1$ between 1 and K, and subsequently select a buffered frame having the sequence number $s=R_1$ as the first one of the N−1 frames. N-frame generation module 204 can then repeat this procedure by generating a second random number $R_2$. If $R_2 \neq R_1$, N-frame generation module 204 can then select the buffered frame having the sequence number $s=R_2$ as the second sampled frame in the N−1 frames. However, if $R_2=R_1$, N-frame generation module 204 is configured to generate a new random number $R_2$ to replace the previous random number $R_2$. These random number generation and comparison steps are repeated until a random number $R_2$ that is not equal to $R_1$ is obtained. At this point, N-frame generation module 204 is configured to select the buffer frame having the sequence number $s=R_2 \neq R_1$ as the second sampled frame of the N−1 frames. Moreover, N-frame generation module 204 is configured to repeat the above procedure of generating a unique random number and selecting a buffered frame having the sequence number s equal to the unique random number, if less than N−1 randomly-sampled frames have been obtained. However, this procedure can be terminated when N−1 randomly-sampled frames based on N−1 unique and randomly-generated numbers have been selected among the K−1 buffered frames.

After N−1 randomly-sampled frames of the endoscope video 208 have been obtained, N-frame generation module 204 is configured to combine the N−1 randomly-sampled frames with the current frame K to obtain a set of N-frames, wherein the set of N-frames are arranged in the temporal order consistent with the corresponding sequence numbers s of the set of N-frames. In other words, the set of N-frames are ordered in ascending order of the corresponding set of sequence numbers s so that the original temporal order of the set of N-frames in the endoscope feed 208 is maintained.

Note that at the beginning of the surgical procedure, the set of N-frames generated by N-frame generation module 204 typically comprises similar images because the N-frames are closely spaces. As the surgical procedure progresses and particular when the real-time procedure progresses toward the end of the surgical procedure, individual frames within the set of N-frames become increasingly more spread out and the set of N-frames become increasingly more different from one another. Consequently, the set of N-frames continues to serve as the proxy of the events that have taken place in the elapsed portion of the surgical procedure.

Also note that the set of N-frames generated by the above-described N-frame generation procedure is to be used to produce a single RSD prediction at the current time T, which itself is a single decision time-point among the sequence of predetermined prediction time-points during the entire surgical procedure. Hence, the above N-frame generation procedure is continuously performed by N-frame generation module 204 at a sequence of RSD prediction time points throughout the live surgical procedure to generate a sequence of randomly-sampled N-frames 214 (note that "a sequence of randomly-sampled N-frames 214" herein means multiple sets of N-frames generated at the sequence of RSD prediction time points and arranged in temporal order). A person skilled in the art will appreciate that as time progresses through the live surgical procedure, the set of buffered video frames K in the frame buffer 210 continues to grow (before reaching a maximum allowed value if such a maximum exists). Consequently, we further designate the set of buffered video frames as K(T), which is a function of the current time T. As such, at each new RSD prediction time-point T, a new set of N-frames is generated based on the new set of buffered video frames K(T) in frame buffer 210.

Note that when comparing two consecutive sets of N frames $\{F_1\}$ and $\{F_2\}$ generated at two consecutive prediction time-points $T_1$ and $T_2>T_1$, two observations can be made. Firstly, each randomly-sampled frame in set $\{F_2\}$ is selected from $K(T_2)$ whereas each randomly sampled frame in set $\{F_1\}$ is selected from $K(T_1)$, and wherein $K(T_2)>K(T_1)$ (before reaching a maximum value $K_{max}$ if such a maximum exists) represents a slightly longer period of the elapsed portion of the surgical procedure. Secondly, a given randomly-sampled frame in set $\{F_2\}$ can also be in set $\{F_1\}$. In other words, the randomness in the random sampling operation allows the same buffered frame in frame buffer 210 to be selected more than once in the sequence of predetermined prediction time-points during the live surgical procedure. This property of the disclosed N-frame generation module 204 allows RSD-prediction system 200 to revisit/reprocess some previously-processed video frames at a later time, which has the benefit of gradually improving RSD prediction stability and consistency.

Returning to FIG. 2, note that RSD-prediction system 200 further includes trained RSD-prediction model 206 which is coupled to N-frame generation module 204. As will be discussed in more detail below, trained RSD-prediction model 206 can be constructed/trained based on a training dataset/datasets that is generated from one or multiple training videos of the same surgical procedure and using the same N-frame generation procedure described above. When performing real-time RSD predictions within RSD-prediction system 200, RSD-prediction model 206 is configured to receive a single set of N-frames at the current prediction time point T among the sequence of randomly-sampled N-frames 214 from N-frame generation module 204, and subsequently generate a new and current RSD prediction based on processing the unique set of N-frames. In some other embodiments, RSD-prediction model 206 is configured to process the set of N-frames based on the corresponding order of the set of frames but without having to know the exact timestamps associated with the set of frames.

In some embodiments, instead of generating just one randomly-selected set of N-frames at a current time point T and computing a single RSD prediction, multiple randomly-selected set of N-frames at the current time point T can be generated and subsequently RSD-prediction model 206 is used to generate multiple RSD predictions based on processing the multiple sets of randomly-selected N-frames corresponding to the same current time point T Next, a variance and an average value of the RSD prediction for the current time point T can be computed based on the multiple RSD predictions corresponding to the current time point T. The current RSD prediction can then be replaced with the computed average and variance values, which represents a more reliable RSD prediction at the current time point T than the single RSD prediction approach.

Note that in addition to making RSD predictions, e.g., as a quantity in minutes, RSD-prediction model 206 can also be configured to generate a percentage-of-completion prediction indicating what percentage of the surgical procedure has been completed at the current time point T. Note that the percentage-of-completion prediction provides another useful piece of information for both the surgical crew in the live session and the surgical crew waiting in line for the next surgical session.

In some embodiments, RSD-prediction ML model 206 can be implemented using various convolutional neural network (CNN/ConvNet) architectures. For example, a particular embodiment of RSD-prediction model 206 is based on using an action recognition network architecture (I3d) as the backbone of the model, which is configured to receive a sequence of video frames as a single input. However, other implementations of RSD-prediction model 206 can also use a recurrent neural network (RNN) architecture, such as a long short-term memory (LSTM) network architecture. During a live surgical procedure, trained RSD-prediction model 206 is configured to generate continuous real-time RSD predictions 216 (e.g., as minutes remaining) at the sequence of predetermined prediction time points based on the sequence of randomly-sampled N-frames 214, so that the surgeon and surgical staff both inside and outside the operating room can be constantly informed of the progress and remaining surgical duration. In some embodiments, as new RSD predictions are continuously generated, a Butterworth filter can be used to "smooth out" the RSD outputs, e.g., by removing some high frequency jitters, so that a set of most recent predictions can be used as an indicator of the direction (e.g., decreasing or increasing in time) of the next RSD prediction.

Note that by sampling the buffered video frames representing the elapsed portion of the surgical procedure at each prediction time point in small time-steps (e.g., 1-second or 2-second) and making a corresponding RSD prediction at each prediction time point, the disclosed RSD-prediction system 200 generates a population of predictions which are separated by the small sampling interval, e.g., 1 second or 2-second apart. Using such small sampling time-steps, the disclosed RSD-prediction system 200 is configured to randomly-sample substantially the same set of buffered video frames over and over again to make a series of similar RSD predictions. Hence, the consistency in the series of RSD predictions is necessary to indicate the effectiveness of RSD-prediction model 206 in making such RSD predictions.

As mentioned above, when the frame buffer 210 size has a limit, buffer management is required as more video frames are added. In a naïve approach, when the buffer size limit is reached, a new video frame added into frame buffer 210 would be accompanied by an older frame, e.g., the oldest frame to be removed from frame buffer 210. However, this approach is not desirable because it would continue to remove the early portion of the surgical procedure, but the disclosed random-sampling technique is intended to sample the entire elapsed portion of the surgical duration at each and every prediction time point. In some embodiments, instead of dropping the oldest video frames from the frame buffer 210, older frames in the buffer may be more strategically removed throughout the entire buffer. For example, a frame removal strategy can include removing every other frame in the buffer, so that the surgical procedure information from the earlier portion of the video can always be preserved. To keep even more video frames from early portion of the video, video frames can also be assigned weights of importance such that older frames receive higher weights while the newer frames receive lower weights. This technique combined with the above-described every-other-frame removal technique can allow even more video frames from the beginning portion of the surgical video to be kept in frame buffer 210 throughout the surgical procedure.

As mentioned above, the predetermined number N should be chosen as a trade-off between the computational constraints for RSD-prediction model 206 to process the set of N-frames (which dictates an upper limit of N) and a sufficiently large set of N–1 randomly-sampled frames from the elapsed portion of the surgical procedure to allow RSD-prediction model 206 to "observe" and hence estimate the progress of the surgical procedure up to the current time/frame based on the current set of N-frames (which dictates a lower limit of N). In one particular embodiment, N=8, i.e., 7-randomly sampled frames plus the current frame for each RSD prediction has been found to provide an optimal balance between the computational complexity and the RSD-prediction accuracy throughout the surgical procedure.

In some embodiments, instead of keeping number N constant throughout a given surgical procedure, it is possible to add more frames by N-frame generation module 204, so that N becomes a variable number to allow more buffered frames to be sampled as the live surgical procedure progresses. However, for the consistency of image processing by the RSD-prediction model 206, a disclosed RSD-prediction system implementing an increasing number of sampled frames would need to start with a set of P frames comprising a set of N-frames followed by a set of M "black frames," wherein each black frame is used as a dummy frame which does not contribute to the decision making. However, as time progresses, e.g., at a set of predetermined time points in the surgical procedure, one or more frames in the set of M black frames will be added onto the set of N-frames to actually sample the real buffered frames. By combining with the original set of N-frames, the newly added frames from the set of M black frames allow more buffered frames to be sampled and processed by RSD-prediction model 206 for real-time RSD predictions.

In some embodiments, RSD-prediction system 200 may choose RSD-prediction model 206 based on the specific surgical procedure. In other words, a number of RSD-prediction models may be constructed for various unique surgical procedures. For example, if the surgical procedure being performed is Roux-en-Y gastric bypass, RSD-prediction system 200 is configured to choose a RSD-prediction model 206 constructed and trained specifically for Roux-en-Y gastric bypass. However, if the surgical procedure being performed is sleeve gastrectomy, RSD-prediction system 200 may choose a different RSD-prediction model 206 constructed and trained for sleeve gastrectomy in RSD-prediction system 200. Hence, prior to using RSD-prediction model 206 in a live surgical procedure for real-time RSD predictions, RSD-prediction model 206 needs to be trained using training videos, e.g., the recorded videos of the same surgical procedure performed by a gold standard surgeon or by a number of surgeons who perform the same surgical procedure in a more or less similar manner.

Figure 3:
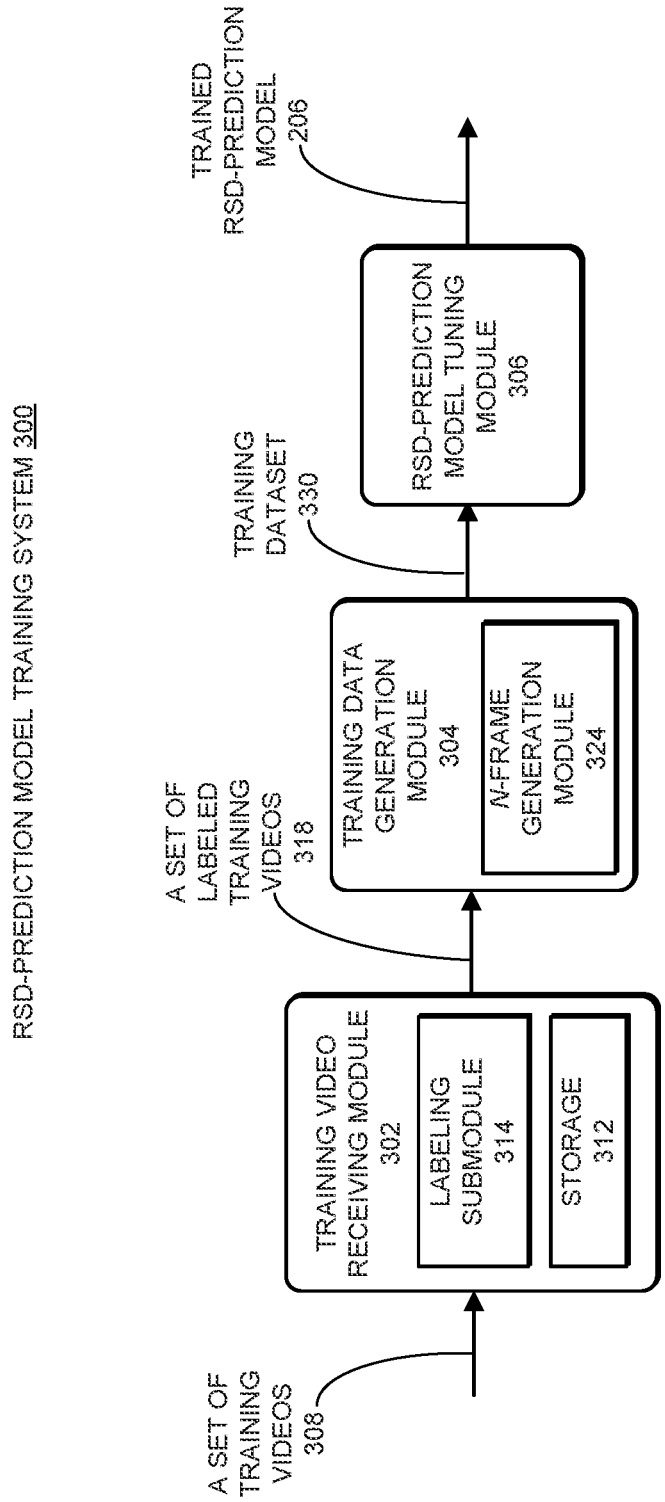
FIG. 3 illustrates a block diagram of an RSD-prediction model training system for constructing the trained RSD-prediction model in the disclosed RSD-prediction system in accordance with some embodiments described herein.

FIG. 3 illustrates a block diagram of an RSD-prediction model training system 300 for constructing RSD-prediction model 206 in RSD-prediction system 200 in accordance with some embodiments described herein. As shown in FIG. 3, RSD-prediction model training system 300 can include a training video receiving module 302, a training data generation module 304, and a RSD-prediction model tuning module 306, which are coupled in the manner shown. Note that the disclosed RSD-prediction model training system 300 (or "model training system 300" hereinafter) is configured to construct/train RSD-prediction model 206 used in RSD-prediction system 200 for a specific surgical procedure including a predetermined set of phases/steps (wherein each phase/step can further include predetermined subphases/substeps). Trained RSD-prediction model 206, which is the output of model training system 300, can then be used for real-time RSD predictions in RSD-prediction system 200 during a live surgical session of the specific surgical procedure, e.g., a Roux-en-Y gastric bypass procedure or a sleeve gastrectomy procedure.

In some embodiments, training video receiving module 302 in model training system 300 receives a set of recorded training videos 308 of the same surgical procedure as RSD-prediction model 206, e.g., a gastric bypass procedure. For example, the set of training videos 308 can include a training video A depicting the surgical procedure being performed by a gold standard surgeon or otherwise a surgeon who is skilled in performing the given surgical procedure in the standard manner. As such, training video A can be used to establish a standard in performing the given surgical procedure when training video A is used to train RSD-prediction model 206. Note that while a single training video of a surgeon skilled in the surgical procedure allows the RSD-prediction model 206 to learn the features of the surgical procedure depicted in that video, it may not be sufficient to teach the model to recognize variations to the standard execution of the surgical procedure, such as variations in the orders of execution of a set of steps in the surgical procedure. Moreover, a single training video also may not be sufficient to teach the model to recognize different types of complications, such as adhesion in patients, and unusual events that can occur during the surgical procedure. However, when multiple training videos that cover various scenarios and variations of the same surgical procedure are used to train RSD-prediction model 206, the trained model becomes more robust with the ability to recognize (1) variations in the order of the surgical steps; (2) patient complications; (3) unusual events; and (4) other variations.

In some embodiments, the set of training videos 308 can include recorded surgical videos of the same surgical procedure performed by a number of surgeons who can perform the surgical procedure in a similar manner, e.g., by performing the same set of standard surgical steps associated with the surgical procedure. However, the set of training videos 308 can also include variations in performing the surgical procedure. In some embodiments, the set of training videos 308 can include a first subset set of recorded videos that captures variations in the order of carrying out the set of surgical steps. The set of training videos 308 can also include a second subset set of recorded videos that captures known patient complications and known types of unusual events that can occur during the same surgical procedure. In some embodiments, the set of training videos 308 can also include the same surgical procedure captured at different camera angels. For example, two training videos can be generated by two endoscope cameras positioned at two opposing angles to capture additional timing information of the surgical procedure not capable of obtaining at a single camera angel.

In some embodiments, training video receiving module 302 can include a storage 312, and training video receiving module 302 is configured to preload the set of training videos 308 into storage 312 prior to the actual model training process. Note that unlike frame buffer 210 described in conjunction with endoscope video receiving module 202, storage 312 can store the entire set of training videos 308 without size restriction. In some embodiments, training video receiving module 302 further includes a labeling submodule 314 configured to label each frame in each received training video in the set of training videos 308 (referred to as "a given training video 308" hereinafter) to associate the frames with respective timing information. In some implementations, labeling submodule 314 is configured to label each frame in the given training video 308 with a sequential frame number, e.g., 0, 1, 2, etc., based on the order of the frames within the given training video 308. Note that this frame-number label can indicate a relative timing of the associated frame in the associated surgical procedure. Note that based on the frame-number label of a given frame, the particular timestamp of the given frame in the associated surgical procedure and the RSD value from the given frame to the end of the surgical procedure can be automatically determined. Inversely, when a timestamp (e.g., 23 min 45 sec) is provided for the given training video 308, the frame-number label associated with the timestamp can be automatically determined and the corresponding video frame can be subsequently selected.

In some embodiments, labeling the given training video 308 in the set of training videos may additionally and optionally include providing surgical phases/steps and/or subphases/substeps labels for the video frames in the given training video 308. For example, if a given surgical phase/step of the surgical procedure in the given training video 308 starts at 20 min 15 sec and ends at 36 min 37 sec, each frame between these two timestamps should be labeled as the same surgical phase/step. Note that this phase/step label for each frame is in addition to the above-described frame-number label of the given frame. In some implementations, these additionally and optionally phase/step labels for the given training video 308 can be generated by human operators/labelers by manually identifying the beginning time-point and the end time-point of each phase/step, and subsequently annotating the frames between the beginning and the end time-points with the associated phase/step label. Hence, in the subsequent parameter tuning steps, the frame-number label of a given frame can be used to determine the particular timestamp for the given frame and the phase/step label of the given frame can be used to determine which phase/step in the associated surgical procedure the given frame is associated with in the given training video 308.

In some other embodiments, the additionally and optionally phase/step labels for the given training video 308 can be generated automatically by labeling submodule 314. For example, labeling submodule 314 may include a separate deep-learning neural network which has been trained for the particular surgical procedure associated with the given training video 308 for phase/step recognitions. Hence, labeling submodule 314 including such a trained deep-learning neural network can be used to automatically identify the beginning and the end of each surgical phase/step in the given training video 308 and subsequently label the frames between the two identified boundaries of a given phase/step with the corresponding phase/step labels. Note that training video receiving module 302 outputs a set of labeled training videos 318 corresponding to the set of received raw training videos 308.

Training video receiving module 302 is coupled to training data generation module 304 in model training system 300. In some embodiments, training data generation module 304 is configured to process the set of labeled training videos 318 to generate a training dataset 330. In some embodiments, each video frame between the start of a labeled training video and the end of the labeled training video in the set of labeled training videos 318 (referred to as "a given labeled training video 318" hereinafter) can be used to generate a single training data point in the training dataset 330. In some embodiments, training data generation module 304 is configured to generate a set of training data points from the given labeled training video 318 by randomly selecting a set of timestamps within the given labeled training video 318 and subsequently constructing a set of training data points corresponding to the set of randomly-selected time stamps. In this manner, training data generation module 304 can generate training dataset 330 by combining multiple sets of training data points generated from the set of labeled training videos 318.

In some embodiments, instead of generating training data points based on a set of randomly-selected timestamps, training data generation module 304 is configured to generate a set of training data points from the given labeled training video 318 at a set of time points based on a predetermined time interval, and subsequently constructing a set of training data points corresponding to the set of time points. For example, training data generation module 304 can generate a set of training data points from the given labeled training video 318 at a set of time points in 1-minute intervals. In some embodiments, training data generation module 304 generates the training dataset 330 as a training data sequence in accordance with the progress of the surgical procedure in the labeled training video 318. More specifically, training data generation module 304 can generate training dataset 330 by progressively outputting a training data point at each time point within labeled training video 318 based on the predetermined time interval.

Similarly to the above-described RSD-prediction process, each selected time point within the given labeled training video 318 for generating a training data point within training dataset 330 corresponds to a labeled video frame within the given labeled training video 318, referred to as the "selected frame" hereinafter. Note that training data generation module 304 also includes an N-frame generation module 324 which is configured to operate in the same manner as N-frame generation module 204 in RSD-prediction system 200. More specifically, to generate a corresponding training data point at the selected time point, N-frame generation module 324 is configured to obtain the selected frame of the given labeled training video 318 at the selected time point. Next, N-frame generation module 324 is configured to generate N−1 additional frames by randomly sampling N−1 "previous" frames from the portion of the labeled training video 318 before the selected frame and during the time period less than at the selected time point, wherein N herein is a predetermined integer number. In other words, the N−1 additional frames can be obtained from the entire labeled training video 318 from the start of the training video until the selected time point Note that due to the randomness in sampling a set of N−1 frames to form a given training data point, there can be different time intervals between these N frames even when they are ordered in the temporal sequence, e.g., 5-min between the first two frames and 10-min between the last two frames, etc. In some embodiments, these N−1 frames may not include any video frame associated with any out-of-body event within the given labeled training video 318.

As mentioned above, the predetermined number N is chosen as a trade-off between the computational constraints to train the RSD-prediction model 206 with the training dataset 330 comprised of sets of generated N-frames (which dictates an upper limit of N) and a sufficiently large number of sampled frames prior to the selected time point/frame to sufficiently represent the progress of the surgical procedure up to the selected time point/frame (which dictates a lower limit of N). In some embodiments, the predetermined number N used by N-frame generation module 324 in model training system 300 is identical to the predetermined number N used by N-frame generation module 204 in RSD-prediction system 200. In one particular embodiment, N=8, i.e., N-frame generation module 324 is configured to generate an 8-frame training data point by obtaining the selected frame at the selected time point and randomly sampling 7 additional frames throughout the portion of the labeled training video 318 before the selected time point. As described above, the randomness in choosing the N−1 additional frames allows the same frame in labeled training video 318 to be selected more than once when generating training dataset 330 during the RSD-prediction model training process.

After processing the set of labeled training videos 318, training data generation module 304 generates training dataset 330 as the output. Referring back to FIG. 3, note that training data generation module 304 is coupled to RSD-prediction model tuning module 306 (or "model tuning module 306" hereinafter), which is configured to tune a set of neural network parameters within RSD-prediction model 206 based on the received training dataset 330 comprising multiple sets of training data points generated from multiple labeled training videos 318, wherein each training data point is further comprised of a set of N-frames ordered by their respective times/frame-number labels in a given labeled training video 318 in a temporal sequence.

In some implementations, an RSD-prediction model training process involves using training data generation module 304 and model tuning module 306 collectively to train the model based on the set of labeled training videos 318 as follows. To begin, a subset of M training videos is randomly selected from the set of labeled training videos 318. This step may be performed by training data generation module 304. Note that sometimes the set of labeled training videos 318 can include a large number (e.g., hundreds) of videos that cannot be all used for model training at the same time. In particular, the number M can be determined based on the computational resource restrictions for processing a single training data point at a given time. In some embodiments, the number M is determined based on the memory limitations of the one or more processors (e.g., one or more graphic processing units (GPUs)) used by model tuning module 306 to process a set of video frames. Note that if the number M turns out to be equal to or greater than the number of videos in the set of labeled training videos 318, then the entire the set of labeled training videos 318 can be selected.

Next, using training data generation module 304, for each of the M selected training videos, a timestamp is randomly selected between the beginning and the end of the given training video. Subsequently, using training data generation module 304, a video frame in the given training video based on the randomly-selected timestamp is selected. Next, for the randomly-selected video frame, N-frame generation module 324 is used to randomly select N−1 additional frames using the above-described N-frame generation techniques, and combine these N−1 additional frames with the randomly-selected video frame to form a set of N-frames for the given training video. Note that the above steps are repeated for the entire set of M selected training videos corresponding to M randomly-selected frames from the M selected training videos. As a result, training data generation module 304 generates M sets of N-frames corresponding to the M selected training videos (e.g., M=16). We refer to these M sets of N-frames as a "batch" of training data, which can be considered as a single training data point in the training data set 330. Note that a variation to the above described steps to generate a single batch of training data is that, instead of randomly selecting one frame from each of the M selected training videos, each frame in the M frames can be randomly selected from the entire set of M selected training videos. In other words, it is possible to select more than one frame from a given video in the set of M selected training videos, while it is also possible that a given video in the set of M selected training videos does not get selected at all.

After a batch of training data is generated as described above, model tuning module 306 is used to process the batch of training data to optimize the model in a process referred to as an "iteration." Specifically, during the iteration, the batch is passed through the neural network of the RSD-prediction model, and errors are estimated and used to update the parameters, such as the weights and biases of the RSD-prediction model, e.g., using an optimization technique such as gradient descent.

Note that the above-described process of generating a single batch of training data and using the batch to update the RSD-prediction model represents a single iteration of the model training process. As such, many such iterations and the RSD-prediction model gets progressively optimized through each iteration in the many iterations. In some embodiments, during the model training process, the RSD-prediction model is evaluated at the end of each given iteration on a validation dataset. If the RSD-prediction error from the trained model on the validation dataset has stabilized or plateaued (e.g., within a predetermined error margin), then the RSD-prediction model training process can be terminated. Otherwise, another new iteration is added to the model training process.

Note that the above-described RSD-prediction model training process is based on randomly-selecting training data points in the set of labeled training videos 318. In some other embodiments, a disclosed RSD-prediction model training process based on model training system 300 can be a progressive training process following the progression of each labeled training video 318 within the set of labeled training videos 318. In this progressive model training process, training dataset 330 can be generated progressively from the beginning of each labeled training video 318 toward the end of the labeled training video 318 based on a predetermined time interval (e.g., at 1-minute) one data point at a time.

More specifically, training data generation module 304 continues to generate training dataset 330 as a sequence of training data points from the beginning of the given labeled training video 318 toward the end of the given labeled training video 318 based on the predetermined time interval (e.g., at 1-second or 1-minute interval). Similarly, to the above-described RSD-prediction process, the time associated with a current training data point being generated in the progressive model training process may be referred to as the "current time" of the model training process. Hence, at the current time, a current frame in the given labeled training video 318 corresponding to the current time is selected. Next, for the selected current frame, N-frame generation module 324 is used to randomly select N−1 additional frames using the above-described N-frame generation techniques, and combine these N−1 additional frames with the current frame to form a set of N-frames, i.e., the current training data point in training dataset 330.

In the same manner as described above, model tuning module 306 continues to use newly generated training data points within training dataset 330 to tune/update the set of neural network parameters based on a sequence of RSD values (i.e., the true RSD values in the given labeled training video 318) associated with the sequence of training data points. Specifically, tuning the set of neural network parameters based on a given generated training data point and the corresponding RSD value involves predicting RSD values using the RSD-prediction model under training to match the corresponding true RSD value. In some embodiments, tuning the set of neural network parameters with the training dataset 330 includes performing a stochastic gradient descent to minimize the RSD prediction errors. After the entire training dataset 330 generated by training data generation module 304 has been processed by model tuning module 306, model training system 300 eventually outputs trained RSD-prediction model 206.

In some embodiments, the disclosed progressive model training process samples labeled training video 318 based on a small time-step (e.g., a few seconds). Because the sequence of training data points within training dataset 330 are separated by this small time-step, the progressive model training process essentially samples substantially the same set of video frames over and over again during a relatively short time period (e.g., 1 minute) and performs a series of model tuning procedures during this short time period based on substantially the same target RSD. Hence, the disclosed model training process also progressive improves the prediction consistency and accuracy of the trained RSD-prediction model 206.

In some embodiments, instead of generating a single training data point at each current time point, multiple training data points may be generated using N-frame generation module 324 at the same current time point. Because the randomness involved in generating each set of N-frames, each of the multiple training data points generated at the same current time point is most likely comprised of a different set of randomly-sampled N−1 frames, and hence a different set of N-frames. However, because these multiple training data points are also associated with the same target RSD value, using them to tune/train the set of neural network parameters at the associated current time point may result in a faster convergence time than using a single training data point at the given time point.

In some embodiments, model tuning module 306 is configured to train the RSD-prediction model using the set of labeled training videos 318. For example, model tuning module 306 may be configured to sequentially process each training video in the set of labeled training videos 318 based on the above-described progressive training process for a single labeled training video 318 to tune the set of neural network parameters, until the entire set of labeled training videos 318 has been processed.

In some embodiments, model tuning module 306 is also configured to use the set of labeled training videos 318 to train RSD-prediction model 206 to make percentage-of-completion predictions indicating what percentage of the surgical procedure has been completed at the current prediction time point. Because the percentage-of-completion value at each prediction time point is known, model tuning module 306 is configured to tune/train the set of neural network parameters to make the percentage-of-completion prediction by RSD-prediction model 206 to meet the actual percentage-of-completion value at the given prediction time point.

Note that the above-described progressive model training process represents one epoch of training, i.e., the selected training data points from the set of labeled training videos 318 are used just once in a single pass. In some embodiments, to ensure convergence of the model training process, the set of labeled training videos 318 is used repeatedly in multiple epochs/passes.

More specifically, multiple sets of training data points may be first generated from the set of labeled training videos 318 based on the predetermined time interval. Next, the RSD-prediction model is trained through multiple epochs using the same sets of training data points. Specifically, in each epoch of training, the same training step is performed by model tuning module 306 using the same sets of training data points which moves the RSD-prediction model one step closer to the convergence. In practice, 20-50 epochs of training based on the same sets of training data points can be performed. This means that for each data point in the multiple sets of training data points, training data generate module 304 is used 20-50 times to perform the same random-sampling procedure for the given data point 20-50 times. As such, in each epoch of the model training process, a unique training dataset 330 is generated based on the same sets of training data points. This is because the random nature of N-frame generation module 324 allows for different epochs of the model training process to use different sets of previous frames/images for each data point in the same sets of training data points.

Note that compared to uniform sampling of previous frames at each time point T, performing RSD-predictions using either the uniform sampling technique or the disclosed random sampling technique may sometime generate relatively similar real-time RSD-predictions results. However, using the disclosed random-sampling technique for RSD-prediction model training can generally achieve significantly better model training results, such as faster speed of convergence than using the uniform-sampling technique, at least because the uniform-sampling technique cannot generate new training dataset when multiple training data points are generated at the same time point T or in different epochs. Moreover, as described above, the randomness in choosing the N−1 additional frames using the disclosed random-sampling technique also has the benefit of allowing the same previous frame in a given training video to be selected more than once in the generated training dataset, thereby allowing the prediction stability of the trained RSD-prediction model to be gradually but more effectively improved.

Note that the disclosed random-sampling technique also provides a mechanism to test the model prediction confidence of a trained RSD-prediction model during real-time RSD predictions. For example, after the trained RSD-prediction model 206 is used to make a first RSD prediction at a given time point T, the N-frame generation technique can be reapplied to randomly sample earlier frames again and the trained RSD-prediction model 206 is used to make a second prediction. The N-frame generation technique can then be used again to randomly sample earlier frames one more time and the trained RSD-prediction model 206 is used to make a third prediction. Next, the multiple RSD predictions can be compared for prediction confidence. If all three predictions are substantially the same (e.g., with differences within a few seconds), then we can be highly confident of RSD-prediction results. However, if the multiple RSD predictions at the time point T generate significantly different results (e.g., when the additional RSD predictions jump up and down around the first RSD prediction), it can be an indication that the trained model is not capable of learning what has happened from the beginning of the surgical procedure up to the time point T. In such scenarios, a manual intervention, and/or post-operative analysis maybe needed to understand what has happened in the surgical procedure.

Figure 4:
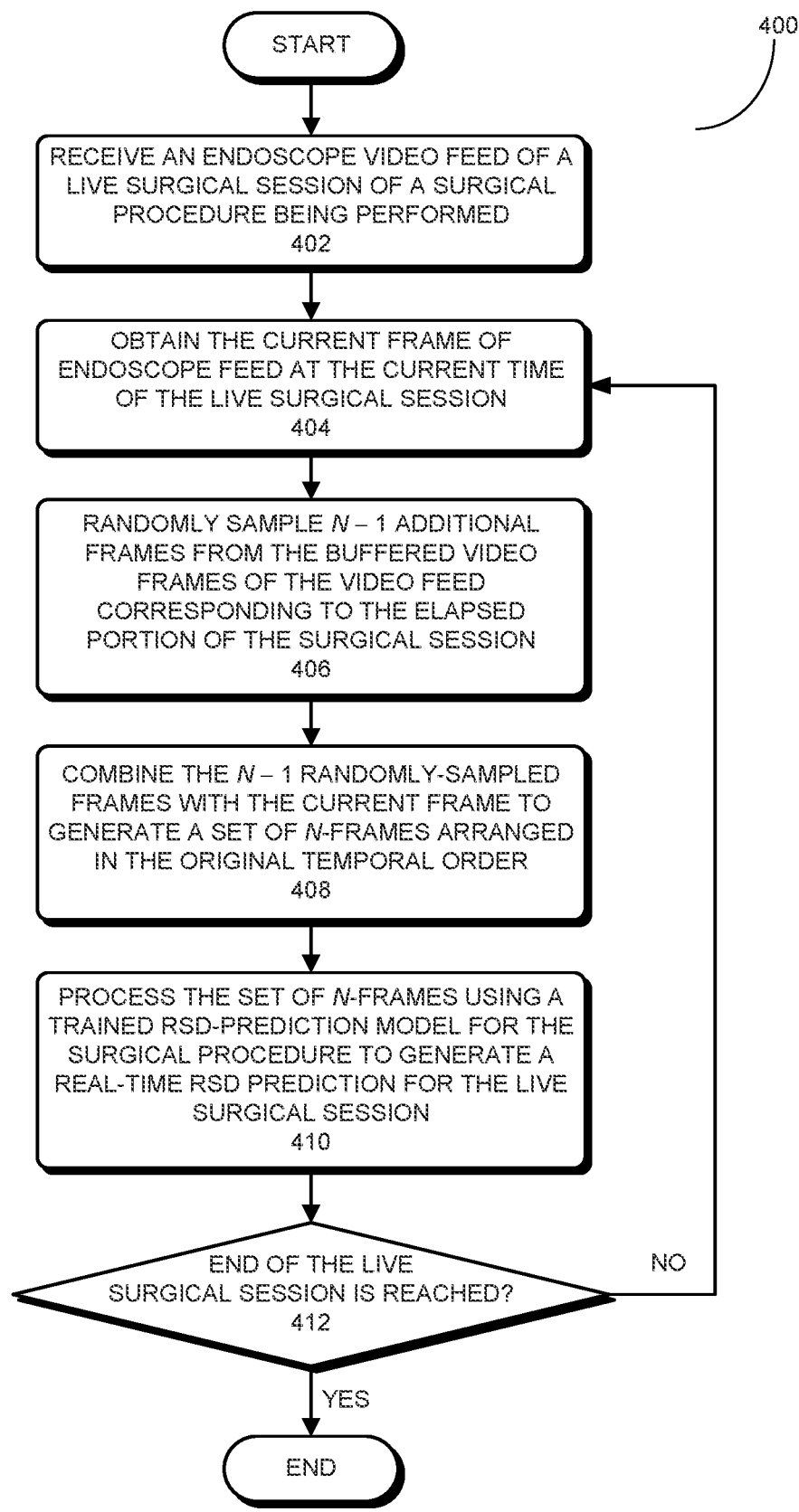
FIG. 4 presents a flowchart illustrating an exemplary process for performing real-time RSD predictions during a live surgical session based on a procedural video feed in accordance with some embodiments described herein.

FIG. 4 presents a flowchart illustrating an exemplary process 400 for performing real-time RSD predictions during a live surgical session based on a procedural video feed in accordance with some embodiments described herein. In one or more embodiments, one or more of the steps in FIG. 4 may be omitted, repeated, and/or performed in a different order. Accordingly, the specific arrangement of steps shown in FIG. 4 should not be construed as limiting the scope of the technique.

Process 400 begins by receiving a real-time/live endoscope video feed of the live surgical session of a particular surgical procedure being performed by a surgeon (step 402). In some embodiments, the surgical procedure is a Roux-en-Y gastric bypass procedure or a sleeve gastrectomy procedure. Next, process 400 obtains the current frame of endoscope feed at the current time of the live surgical session (step 404). Process 400 also randomly samples N−1 additional frames from the stored/buffered video frames of the video feed corresponding to the elapsed portion of the surgical session (step 406). Various embodiments of randomly sampling the N−1 additional frames have been described above in conjunction with RSD-prediction system 200 and FIG. 2. Note that the N−1 randomly-sampled frames from the elapsed portion of the surgical session provides a representative snapshot of a set of events that have taken place during the elapsed portion of the surgical session. Subsequently, process 400 combines the N−1 randomly-sampled frames with the current frame to generate a set of N-frames arranged in the original temporal order (step 408). Next, process 400 processes the set of N-frames using a trained RSD-prediction model for the surgical procedure to generate a real-time RSD prediction for the live surgical session (step 410). Process 400 next determines if the end of the live surgical session is reached (step 412). If not, process 400 subsequent returns to step 404 to continue to process the live video feed at the next prediction time point and generate the next real-time RSD prediction. The real-time RSD prediction process 400 terminates when the end of the live surgical session is reached.

Figure 5:
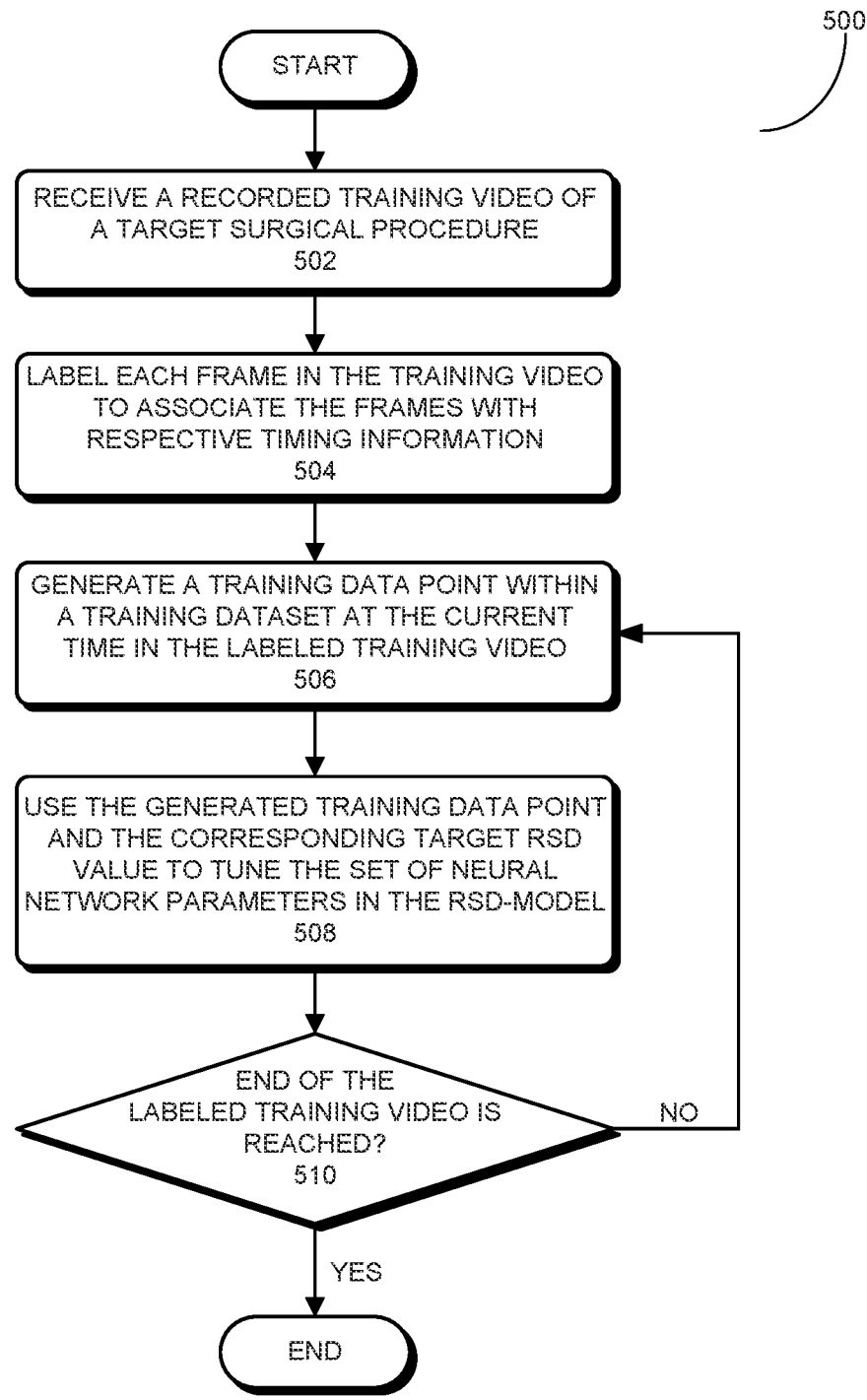
FIG. 5 presents a flowchart illustrating an exemplary process for constructing the trained RSD-prediction model in the disclosed RSD-prediction system in accordance with some embodiments described herein.

FIG. 5 presents a flowchart illustrating an exemplary process 500 for constructing the trained RSD-prediction model in the disclosed RSD-prediction system in accordance with some embodiments described herein. In one or more embodiments, one or more of the steps in FIG. 5 may be omitted, repeated, and/or performed in a different order. Accordingly, the specific arrangement of steps shown in FIG. 5 should not be construed as limiting the scope of the technique.

Process 500 begins by receiving a recorded training video of a target surgical procedure, e.g., a gastric bypass procedure (step 502). In some embodiments, the target surgical procedure is a Roux-en-Y gastric bypass procedure or a sleeve gastrectomy procedure. In some embodiments, the target surgical procedure depicted in the training video is performed by a gold standard surgeon or otherwise a surgeon who is skilled in performing the given surgical procedure in the standard manner. Next, process 500 labels each frame in the received training video to associate the frames with respective timing information (step 504). In some embodiments, the timing information is a sequential frame number based on the order of the frames within the training video. In some implementations, process 500 may additionally and optionally label the set of frames in the training video with surgical phases/steps labels.

Next, process 500 goes through a progressive and semi-supervised learning process following the progression of the labeled training video. Specifically, process 500 generates a training data point within the training dataset at the current time T in the labeled training video (step 506). In some embodiments, process 500 generates the training data point at the current time T by first obtaining the current frame of the labeled training video at the current time T. Next, process 500 generates N−1 additional frames by randomly sampling N−1 "previous" frames from the portion of the labeled training video prior to the current time T. Process 500 subsequently combines the N−1 randomly-sampled frames with the current frame arranged in the original temporal order to obtain the corresponding training data point at the current time T.

Process 500 then uses the generated training data point at the current time and the corresponding target RSD value to tune the set of neural network parameters in the RSD-prediction model (step 508). In some embodiments, tuning the set of neural network parameters based on the given generated training data point and the corresponding target RSD involves using the RSD-prediction model under training to predict RSD values to meet the corresponding target RSD value. Process 500 next determines if the end of the labeled training video is reached (step 510). If not, process 500 subsequent returns to step 506 to continue the progressive training process by generating the next training data point within the training dataset at the next current time T in the labeled training video based on a predetermined time interval. The progressive training process 500 terminates when the end of the labeled training video is reached.

Note that while we have described process 500 based on using a single training video, process 500 can be readily modified to include multiple training videos in accordance with some embodiments described in conjunction with model training system 300 in FIG. 3. Moreover, while the model training process in process 500 is described in the manner of a single epoch, process 500 can be readily modified into a multiple-epoch model training process in accordance with some embodiments described in conjunction with model training system 300 in FIG. 3.

Figure 6:
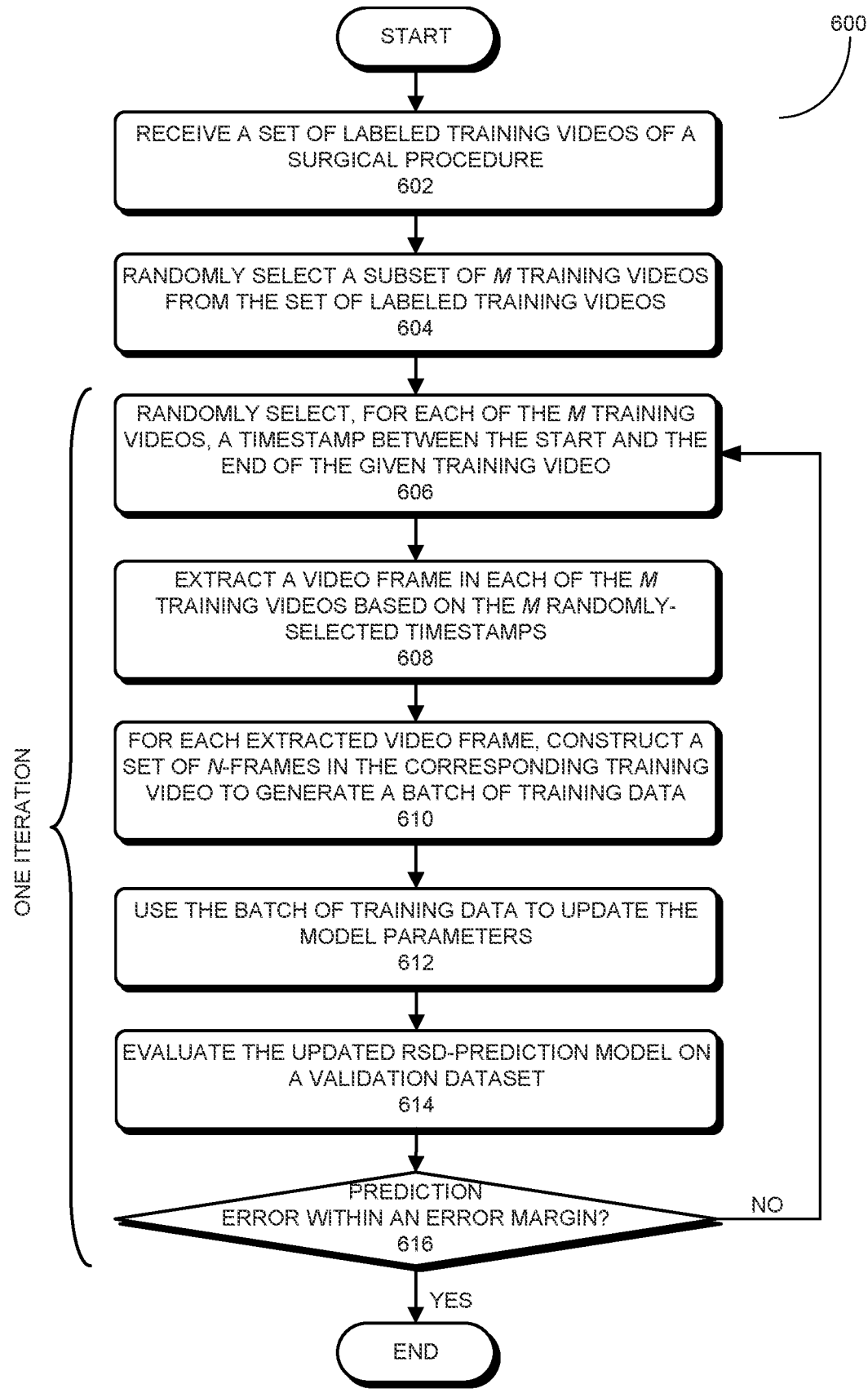
FIG. 6 presents a flowchart illustrating another exemplary process for training a RSD-prediction model in the disclosed RSD-prediction system in accordance with some embodiments described herein.

FIG. 6 presents a flowchart illustrating another exemplary process 600 for training a RSD-prediction model in the disclosed RSD-prediction system in accordance with some embodiments described herein. In one or more embodiments, one or more of the steps in FIG. 6 may be omitted, repeated, and/or performed in a different order. Accordingly, the specific arrangement of steps shown in FIG. 6 should not be construed as limiting the scope of the technique.

Process 600 begins by receiving a set of labeled training videos of a target surgical procedure, e.g., a gastric bypass procedure (step 602). In some embodiments, the set of labeled training videos can include recorded surgical videos of the target surgical procedure performed by a number of surgeons who can perform the target surgical procedure in a similar manner, e.g., by performing the same set of standard surgical steps. However, the set of labeled training videos can also include variations in performing the target surgical procedure, such as variations in the order of carrying out the set of surgical steps. In some embodiments, the set of labeled training videos was obtained from a set of corresponding raw training videos using the above-described training video labeling techniques. In particular, each labeled training video includes timestamps for the associated video frames. In some embodiments, the timestamps for the video frames are represented by a set of frame-number labels.

Next, process 600 randomly selects a subset of M training videos from the set of labeled training videos (step 604). In some embodiments, the number M can be determined based on the computational resource restrictions for processing multiple training data points at a given time. In particular, the number M can be determined based on the memory limitations of the one or more processors (e.g., one or more graphic processing units (GPUs)) used by the system to train the RSD-prediction model. Process 600 subsequently begins an iterative model tuning procedure based on the M selected training videos.

Specifically, in a given iteration of the model tuning procedure, process 600 randomly selects, for each of the M training videos, a timestamp between the beginning and the end of the given training video (step 606). Note that because the frame-number label and the corresponding actual timestamp within a labeled training video are uniquely related to each other, the random timestamp in step 606 can be provided in the form of either the frame number or the actual time. Subsequently, process 600 extracts a video frame in each of the M training videos based on the M randomly-selected timestamps associated with the M training videos (step 608). Next, for each of the M randomly-selected video frames in each of the M training videos, process 600 constructs a set of N-frames for the given video frame in the corresponding training video using the above-described N-frame generation techniques (step 610). As a result, process 600 generates a batch of training data comprising M sets of N-frames extracted from the M training videos.

Subsequently, process 600 uses the batch of training data to update the model parameters, such as the weights and biases of the RSD-prediction model (step 612). For example, process 600 can use an optimization technique such as gradient descent in training the model parameters based on the batch of training data. Next, process 600 evaluates the updated RSD-prediction model on a validation dataset (step 614). Process 600 subsequently determines if the RSD-prediction error from the trained model has reached a plateau or within an acceptable error margin (step 616). If not, process 600 returns to step 606 to start a new iteration of the RSD-prediction model training process. Otherwise, the RSD-prediction model training process 600 terminates.

Additional Benefits and Applications

Note that for OR scheduling purposes, the current surgical procedure is typically allocated with a scheduled OR time based on a statistical average duration, wherein the current surgical procedure is followed by the next scheduled surgical procedure. Conventional RSD prediction techniques are typically more accurate at the beginning of the surgical procedure because early RSD predictions would not be very different from the scheduled OR time. However, the RSD prediction errors would typically increase toward the end of the surgical procedure because the effects of various complication factors and unusual events become increasingly more noticeable in the RSD predictions toward the end of the surgical procedure.

In contrast, real-time RSD predictions generated by the disclosed RSD-prediction model 206 become increasingly more accurate toward the end of the surgical procedure, and the accurate RSD predictions near the end of the surgical procedure can be used by the next surgical crew to get ready. For example, for a 2-hour long surgical procedure, the RSD prediction accuracy would continue to increase in the final half hour of the surgical procedure toward the end of the surgical procedure. This property of the disclosed RSD-prediction system and technique provides the surgeon and surgical crew of the next scheduled surgical procedure highly-reliable RSD predictions near the end of the ongoing surgical procedure, e.g., when the RSD predictions are under 30 minutes. Hence, the surgeon of the next scheduled surgical procedure would know precisely when the current surgical procedure will end so that she/her can get ready and plan a time buffer to arrive at the OR accordingly.

Alternatively, the surgical crew can start preparing for the next scheduled surgical procedure when the real-time RSD prediction equals a predetermined time buffer for preoperative preparations. In other words, accurate RSD predictions allow for performing the preoperative preparations for the next scheduled surgical procedure when the current surgical procedure is still ongoing. For example, when the RSD predictions have reached 20-minute mark, the surgical crew can begin preparing the OR for the next scheduled surgical procedure, but not waiting for the final minutes of the current surgical procedure. This would allow a seamless transition from the current surgical procedure to the next scheduled surgical procedure with a very short gap or no gap between them.

Note that an ideal RSD prediction curve as a function of time would look like a negative sloped line with linearly decreasing y-values with time, i.e., decreasing RSD values. In many circumstances, the actual RSD predictions often follow the ideal prediction curve. However, in some circumstances, various abnormal events can cause the actual RSD predictions to significantly deviate from the ideal RSD prediction curve. One type of abnormal events during the surgical procedure is due to the occurrences of complications associated with difficult anatomies. Another type of abnormal events is due to the occurrences of unusual events such as bleeding or camera view blocking (e.g., due to fogging or blood coverage). The occurrences of the abnormal events usually add extra times/delays into the surgical procedure.

In some embodiments, the disclosed RSD prediction techniques are configured to predict delays caused by abnormal events which are reflected in the RSD prediction outputs/curve to suddenly deviate (e.g., to jump up) from a standard RSD prediction curve (e.g., generated by a gold standard surgeon). The disclosed RSD prediction techniques facilitate automatically and instantly identifying such complication events and other anomalies/unusual events early on or at the beginning of such events based on the real-time RSD prediction outputs. For example, the real-time RSD prediction outputs may cause a sudden change in the slope of the real-time RSD prediction curve, indicating a potential complication. As another example, the RSD prediction curve can be used to identify when a surgeon is switching the order of the surgical procedure by noticing that the prediction outputs suddenly jumps up and subsequently drops back down to follow the general slope of RSD prediction curve. Note that the ability to identify such abnormal events instantly and in real-time allows for identifying a potential problem during the surgical procedure which would necessitate outside assistant.

Another benefit is to compare two surgeons performing the same surgical procedure. We can train the model on a highly skilled, gold standard surgeon on the surgical procedures. We subsequently apply the trained model on another surgeon who is in training to be like the gold standard surgeon. You can then compare the overall RSD curve of the gold standard surgeon (also referred to as "gold standard RSD curve") against the overall RSD curve from the surgeon in training to identify those places in the training RSD curve where the surgeon in training becomes faster or slower than the gold standard curve, as the training RSD curve speeds up and slows down through the surgical procedure. Such comparisons allow the surgeon in training to perform post-operative review of RSD predictions outputs.

Figure 7:
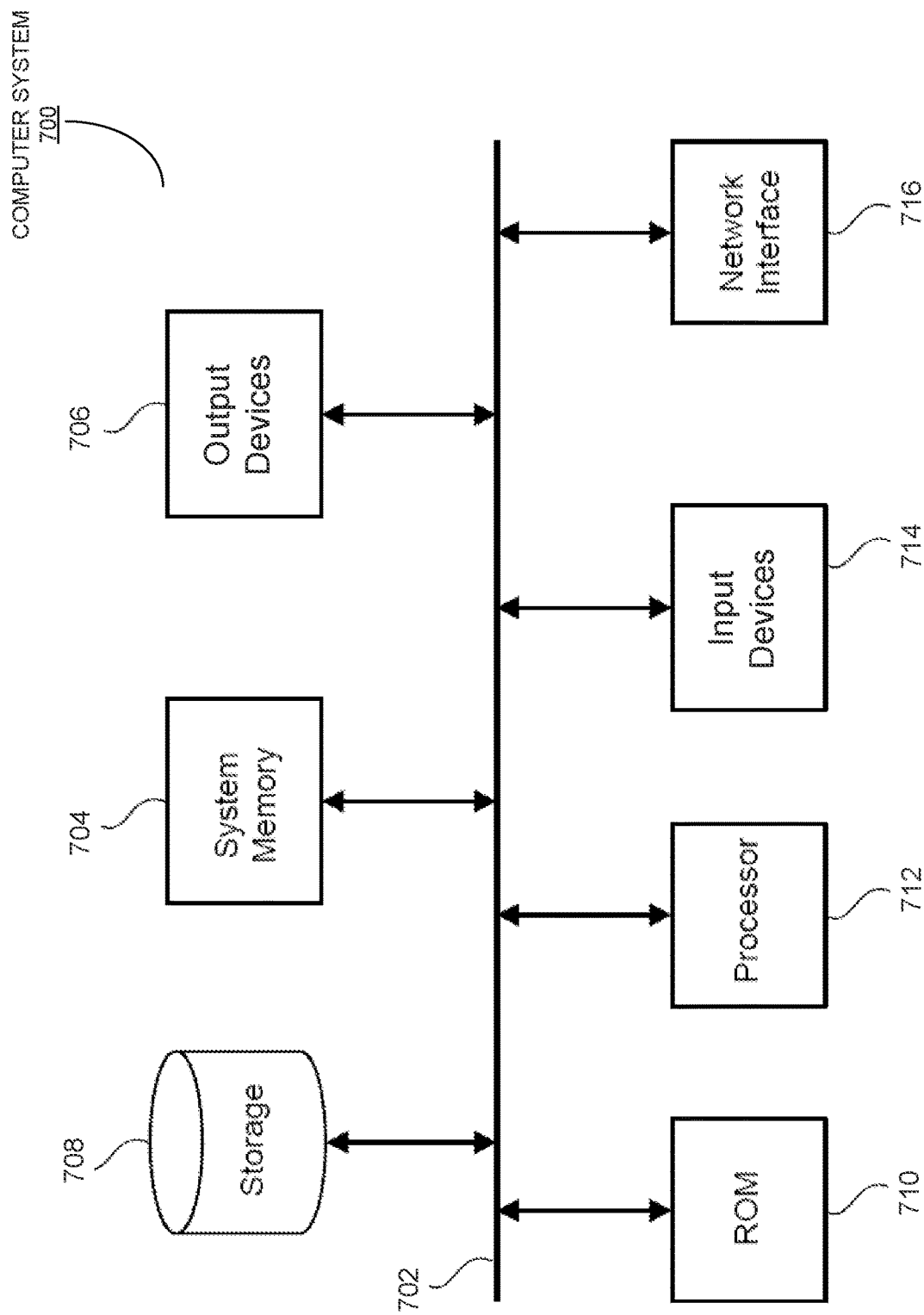
FIG. 7 conceptually illustrates a computer system with which some embodiments of the subject technology can be implemented.

FIG. 7 conceptually illustrates a computer system with which some embodiments of the subject technology can be implemented. Computer system 700 can be a client, a server, a computer, a smartphone, a PDA, a laptop, or a tablet computer with one or more processors embedded therein or coupled thereto, or any other sort of computing device. Such a computer system includes various types of computer-readable media and interfaces for various other types of computer-readable media. Computer system 700 includes a bus 702, processing unit(s) 712, a system memory 704, a read-only memory (ROM) 710, a permanent storage device 708, an input device interface 714, an output device interface 706, and a network interface 716. In some embodiments, computer system 700 is a part of a robotic surgical system.

Bus 702 collectively represents all system, peripheral, and chipset buses that communicatively connect the numerous internal devices of computer system 700. For instance, bus 702 communicatively connects processing unit(s) 712 with ROM 710, system memory 704, and permanent storage device 708.

From these various memory units, processing unit(s) 712 retrieves instructions to execute and data to process in order to execute various processes described in this patent disclosure, including the various real-time RSD-prediction procedures and various RSD-prediction-model training procedures described in conjunction with FIGS. 2-6. The processing unit(s) 712 can include any type of processor, including but not limited to, a microprocessor, a graphic processing unit (GPU), a tensor processing unit (TPU), an intelligent processor unit (IPU), a digital signal processor (DSP), a field-programmable gate array (FPGA), and an application-specific integrated circuit (ASIC). Processing unit(s) 712 can be a single processor or a multi-core processor in different implementations.

ROM 710 stores static data and instructions that are needed by processing unit(s) 712 and other modules of the computer system. Permanent storage device 708, on the other hand, is a read-and-write memory device. This device is a non-volatile memory unit that stores instructions and data even when computer system 700 is off. Some implementations of the subject disclosure use a mass-storage device (such as a magnetic or optical disk and its corresponding disk drive) as permanent storage device 708.

Other implementations use a removable storage device (such as a floppy disk, flash drive, and its corresponding disk drive) as permanent storage device 708. Like permanent storage device 708, system memory 704 is a read-and-write memory device. However, unlike storage device 708, system memory 704 is a volatile read-and-write memory, such as a random access memory. System memory 704 stores some of the instructions and data that the processor needs at runtime. In some implementations, various processes described in this patent disclosure, including the various real-time RSD-prediction procedures and various RSD-prediction-model training procedures described in conjunction with FIGS. 2-6, are stored in system memory 704, permanent storage device 708, and/or ROM 710. From these various memory units, processing unit(s) 712 retrieves instructions to execute and data to process in order to execute the processes of some implementations.

Bus 702 also connects to input and output device interfaces 714 and 706. Input device interface 714 enables the user to communicate information to and select commands for the computer system. Input devices used with input device interface 714 include, for example, alphanumeric keyboards and pointing devices (also called "cursor control devices"). Output device interface 706 enables, for example, the display of images generated by computer system 700. Output devices used with output device interface 706 include, for example, printers and display devices, such as cathode ray tubes (CRT) or liquid crystal displays (LCD). Some implementations include devices such as a touchscreen that functions as both input and output devices.

Finally, as shown in FIG. 7, bus 702 also couples computer system 700 to a network (not shown) through a network interface 716. In this manner, the computer can be a part of a network of computers (such as a local area network ("LAN"), a wide area network ("WAN"), an intranet, or a network of networks, such as the Internet. Any or all components of computer system 700 can be used in conjunction with the subject disclosure.

The various illustrative logical blocks, modules, circuits, and algorithm steps described in connection with the embodiments disclosed in this patent disclosure may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The hardware used to implement the various illustrative logics, logical blocks, modules, and circuits described in connection with the aspects disclosed herein may be implemented or performed with a general purpose processor, a digital signal processor (DSP), an application-specific integrated circuit (ASIC), a field-programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of receiver devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In one or more exemplary aspects, the functions described may be implemented in hardware, software, firmware, or any combination thereof. If implemented in software, the functions may be stored as one or more instructions or code on a non-transitory computer-readable storage medium or non-transitory processor-readable storage medium. The steps of a method or algorithm disclosed herein may be embodied in processor-executable instructions that may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include RAM, ROM, EEPROM, flash memory, CD-ROM or other optical disk storage, magnetic disk storage or other magnetic storage devices, or any other medium that may be used to store desired program code in the form of instructions or data structures and that may be accessed by a computer. The terms "disk" and "disc," as used herein, include compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer-program product.

While this patent document contains many specifics, these should not be construed as limitations on the scope of any disclosed technology or of what may be claimed, but rather as descriptions of features that may be specific to particular embodiments of particular techniques. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can, in some cases, be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described, and other implementations, enhancements and variations can be made based on what is described and illustrated in this patent document.

What is claimed is:

1. A computer-implemented method for continuously predicting in real-time a remaining surgical duration (RSD) of a live surgical session of a surgical procedure based on a real-time endoscope video of the live surgical session, the method comprising:
    receiving a current frame of the endoscope video at a current time of the live surgical session, wherein the current time is among a sequence of prediction time points for making continuous RSD predictions during the live surgical session;
    randomly sampling N−1 additional frames of the endoscope video corresponding to the elapsed portion of the live surgical session between the beginning of the endoscope video corresponding to the beginning of the live surgical session and the current frame corresponding to the current time;
    combining the N−1 randomly sampled frames and the current frame in the temporal order to obtain a set of N frames;
    feeding the set of N frames into a trained RSD machine-learning (ML) model for the surgical procedure; and
    outputting a current RSD prediction from the trained RSD ML model based on the set of N frames.

2. The computer-implemented method of claim 1, wherein N is chosen to be sufficiently large so that the N−1 randomly-sampled frames provide a sufficiently accurate snapshot of various events that have occurred during the elapsed portion of the live surgical session.

3. The computer-implemented method of claim 1, wherein randomly sampling the elapsed portion of the live surgical session allows for sampling a given frame in the endoscope video more than once at different prediction time points while making continuous RSD predictions.

4. The computer-implemented method of claim 1, wherein the method further comprises generating a prediction of a percentage of completion of the live surgical session using the trained RSD ML model based on the set of N frames.

5. The computer-implemented method of claim 1, wherein the method further comprises improving the current RSD prediction at the current time by:
    repeating the following steps multiple times to generate a set of current RSD predictions:
        randomly sampling N−1 additional frames of the endoscope video corresponding to the elapsed portion of the live surgical session between the beginning of the endoscope video corresponding to the beginning of the live surgical session and the current frame corresponding to the current time;
        combining the N−1 randomly sampled frames and the current frame in the temporal order to obtain a set of N frames;
        feeding the set of N frames into a trained RSD ML model; and
        generating a current RSD prediction from the trained RSD ML model based on the set of N frames; and
    computing an average value and a variance value of the set of current RSD predictions; and
    improving the current RSD prediction by using the computed average and variance values as the current RSD prediction.

6. The computer-implemented method of claim 1, wherein the method further comprises improving the RSD predictions by:
    generating a continuous sequence of real-time RSD predictions corresponding to the sequence of prediction time points in the endoscope video; and
    applying a low-pass filter to the sequence of real-time RSD predictions to smooth out the RSD predictions by removing high frequency jitters in the sequence of real-time RSD predictions.

7. The computer-implemented method of claim 1, wherein the method further comprises generating a training dataset by:
    receiving a set of training videos of the surgical procedure, wherein each video in the set of training videos corresponds to an execution of the surgical procedure performed by a surgeon skilled in the surgical procedure;
    for each training video in the set of training videos, constructing a set of labeled training data by performing a sequence of training data generation steps at a sequence of equally-spaced time points throughout the training video according to a predetermined time-interval, wherein each training data generation step in the sequence of training data generation steps at a corresponding time point in the sequence of time points includes:
        receiving a current frame of the training video at the corresponding time point;
        randomly sampling N−1 additional frames of the training video corresponding to the elapsed portion of the surgical session between the beginning of the training video and the current frame;
        combining the N−1 randomly sampled frames and the current frame in the temporal order to obtain a set of N frames; and
        labeling the set of N frames with a label associated with the current frame; and
    outputting multiple sets of labeled training data associated with the set of training videos.

8. The computer-implemented method of claim 7, wherein the method further comprises establishing the trained RSD ML model by:
    receiving a convolutional neural network (CNN) model;
    training the CNN model with the training dataset comprising the multiple sets of labeled training data; and
    obtaining the trained RSD ML model based on the trained CNN model.

9. The computer-implemented method of claim 7, wherein prior to generating the training dataset, the method further comprises labeling each training video in the set of training videos by:
    for each video frame in the training video, automatically determining a remaining surgical duration from the video frame to the end of the training video; and automatically annotating the video frame with the determined remaining surgical duration as the label of the video frame.

10. The computer-implemented method of claim 7, wherein the label associated with the current frame includes an associated remaining surgical duration in minutes.

11. The computer-implemented method of claim 8, wherein the CNN model includes an action recognition network architecture (I3d) configured to receive a sequence of video frames as a single input.

12. The computer-implemented method of claim 8, wherein training the CNN model with the training dataset includes evaluating the CNN model on a validation dataset.

13. A system for continuously predicting in real-time a remaining surgical duration (RSD) of a live surgical session of a surgical procedure based on a real-time endoscope video of the live surgical session, the method comprising, the system comprising:

one or more processors; and a memory coupled to the one or more processors, wherein the memory stores instructions that, when executed by the one or more processors, cause the system to:

receive a current frame of the endoscope video at a current time of the live surgical session, wherein the current time is among a sequence of prediction time points for making continuous RSD predictions during the live surgical session;

randomly sample N−1 additional frames of the endoscope video corresponding to the elapsed portion of the live surgical session between the beginning of the endoscope video corresponding to the beginning of the live surgical session and the current frame corresponding to the current time;

combine the N−1 randomly sampled frames and the current frame in the temporal order to obtain a set of N frames;

feed the set of N frames into a trained RSD machine-learning (ML) model for the surgical procedure; and output a current RSD prediction from the trained RSD ML model based on the set of N frames.

14. The system of claim 13, wherein N is chosen to be sufficiently large so that the N−1 randomly-sampled frames provide a sufficiently accurate snapshot of various events that have occurred during the elapsed portion of the live surgical session.

15. The system of claim 13, wherein the memory further stores instructions that, when executed by the one or more processors, cause the system to improve the current RSD prediction at the current time by:

repeating the following steps multiple times to generate a set of current RSD predictions:

randomly sampling N−1 additional frames of the endoscope video corresponding to the elapsed portion of the live surgical session between the beginning of the endoscope video corresponding to the beginning of the live surgical session and the current frame corresponding to the current time;

combining the N−1 randomly sampled frames and the current frame in the temporal order to obtain a set of N frames;

feeding the set of N frames into a trained RSD ML model; and generating a current RSD prediction from the trained RSD ML model based on the set of N frames; and computing an average value and a variance value of the set of current RSD predictions; and improving the current RSD prediction by using the computed average and variance values as the current RSD prediction.

16. The system of claim 13, wherein the memory further stores instructions that, when executed by the one or more processors, cause the system to improve the RSD predictions by:

generating a continuous sequence of real-time RSD predictions corresponding to the sequence of prediction time points in the endoscope video; and applying a low-pass filter to the sequence of real-time RSD predictions to smooth out the RSD predictions by removing high frequency jitters in the sequence of real-time RSD predictions.

17. The system of claim 13, wherein the memory further stores instructions that, when executed by the one or more processors, cause the system to generate a training dataset by:

receiving a set of training videos of the surgical procedure, wherein each video in the set of training videos corresponds to an execution of the surgical procedure performed by a surgeon skilled in the surgical procedure;

for each training video in the set of training videos, constructing a set of labeled training data by performing a sequence of training data generation steps at a sequence of equally-spaced time points throughout the training video according to a predetermined time-interval, wherein each training data generation step in the sequence of training data generation steps at a corresponding time point in the sequence of time points includes:

receiving a current frame of the training video at the corresponding time point;

randomly sampling N−1 additional frames of the training video corresponding to the elapsed portion of the surgical procedure between the beginning of the training video and the current frame;

combining the N−1 randomly sampled frames and the current frame in the temporal order to obtain a set of N frames; and labeling the set of N frames with a label associated with the current frame; and outputting multiple sets of labeled training data associated with the set of training videos.

18. The system of claim 17, wherein the memory further stores instructions that, when executed by the one or more processors, cause the system to establish the trained RSD ML model by:

receiving a convolutional neural network (CNN) model;

training the CNN model with the training dataset comprising the multiple sets of labeled training data corresponding to the set of training videos; and obtaining the trained RSD ML model based on the trained CNN model.

19. The system of claim 18, wherein the memory further stores instructions that, when executed by the one or more processors, cause the system to train the CNN model with the multiple sets of labeled training data by:

randomly selecting one labeled training data from each set of labeled training data in the multiple sets of labeled training data;

combining the set of randomly-selected labeled training data to form a batch of training data; and training the CNN model with the batch of training data to update the CNN model.

20. The system of claim 18, wherein the CNN model includes an action recognition network architecture (I3d) configured to receive a sequence of video frames as a single input.

\* \* \* \* \*